(12) United States Patent
Yan et al.

(10) Patent No.: US 9,546,387 B2
(45) Date of Patent: Jan. 17, 2017

(54) MICROBIAL PRODUCTION OF MUCONIC ACID AND SALICYLIC ACID

(71) Applicant: University of Georgia Research Foundation, Inc., Athens, GA (US)

(72) Inventors: Yajun Yan, Bogart, GA (US); Yuheng Lin, Bogart, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 14/622,155

(22) Filed: Feb. 13, 2015

(65) Prior Publication Data
US 2015/0225751 A1 Aug. 13, 2015

Related U.S. Application Data

(60) Provisional application No. 61/939,593, filed on Feb. 13, 2014.

(51) Int. Cl.
| | | |
|---|---|---|
| C12P 7/44 | (2006.01) | |
| C12P 7/42 | (2006.01) | |
| C12N 9/88 | (2006.01) | |
| C12N 9/90 | (2006.01) | |

(52) U.S. Cl.
CPC . *C12P 7/44* (2013.01); *C12N 9/88* (2013.01); *C12N 9/90* (2013.01); *C12P 7/42* (2013.01); *C12Y 402/99021* (2013.01); *C12Y 504/04002* (2013.01); *Y02P 20/52* (2015.11)

(58) Field of Classification Search
None
See application file for complete search history.

(56) References Cited

U.S. PATENT DOCUMENTS

| | | |
|---|---|---|
| 5,616,496 A | 4/1997 | Frost et al. |
| 2014/0370557 A1 | 12/2014 | Yan et al. |

FOREIGN PATENT DOCUMENTS

| | | | |
|---|---|---|---|
| WO | WO 2015/031048 | * | 3/2015 |

OTHER PUBLICATIONS

American Type Culture Collection, "ATTC No. 31884," Product Sheet: Organism: *Escherichia coli*; Designation: NST 74 [online]; Manassas, VA [retrieved on Mar. 14, 2016] from the Internet. <URL: atcc.org/products/all/31884.aspx#documentation >; 2 pgs.
National Center for Biotechnology Information, National Library of Medicine, National Institutes of Health, GenBank Locus NZ_CP009273, Accession No. NZ_CP009273, "*Escherichia coli* BW25113, complete genome," [online]. Bethesda, MD [retrieved on Mar. 14, 2016]. Retrieved from the Internet: <URL: ncbi.nlm.nih.gov/nuccore/NZ_CP009273.1 >; 391 pgs.
National Center for Biotechnology Information, National Library of Medicine, National Institutes of Health, GenBank Locus NC_002947, Accession No. NC_002947, "*Pseudomonas putida* KT2440 complete genome," [online]. Bethesda, MD [retrieved on Mar. 22, 2016]. Retrieved from the Internet: <URL: ncbi.nlm.nih.gov/nuccore/NC_002947.4>; 91 pgs.
SF2575 National Center for Biotechnology Information, National Library of Medicine, National Institutes of Health, GenBank Locus GQ409537, Accession No. GQ409537, "*Streptomyces* sp. SF2575 SF2575 gene cluster, complete sequence," [online]. Bethesda, MD [retrieved on Mar. 22, 2016]. Retrieved from the Internet: <URL: ncbi.nlm.nih.gov/nuccore/GQ409537.1>; 24 pgs.
Ajikumar et al. "Isoprenoid Pathway Optimization for Taxol Precursor Overproduction in *Escherichia coli*" *Science*, Oct. 1, 2010; 330(6000):70-4.
Anthony et al. "Optimization of the mevalonate-based isoprenoid biosynthetic pathway in *Escherichia coli* for production of the anti-malarial drug precursor amorpha-4,11-diene" *Metab. Eng.* Jan. 2009; 11(1):13-9.
Atsumi et al. "Non-fermentative pathways for synthesis of branched-chain higher alcohols as biofuels" *Nature*, Jan. 3, 2008; 451(7174):86-9.
Atsumi et al., "Metabolic engineering of *Escherichia coli* for 1-butanol production" Metab. Eng., 2008; 10:305-11.
Beinema et al. "Pharmacogenetic differences between warfarin, acenocoumarol and phenprocoumon" *Thromb. Haemos.*, Dec. 2008; 100(6):1052-7.
Bera et al. "Structure of PqsD, a Pseudomonas quinolone signal biosynthetic enzyme, in complex with anthranilate" *Biochemistry (Mosc.)* Sep. 15, 2009; 48(36):8644-55.
Beuerle et al., "Purification and characterization of benzoate:coenzyme A ligase from *Clarkia breweri*" *Arch. Biochem. Biophys.* 2002; 400(2):258-64.
Bond-Watts et al. "Enzyme mechanism as a kinetic control element for designing synthetic biofuel pathways" *Nat. Chem. Biol.* Apr. 2011; 7(4):222-7.
Bye et al. "The biosynthesis of 4-hydroxycoumarin and dicoumarol by *Aspergillus fumigatus* Fresenius" *Biochem. J.* 1970; 117(2):237-45.
Chen et al. "Biosynthesis of salicylic acid in plants" *Plant Signal Behav.* 2009; 4(6):493-6.
Cohen et al. "Venous thromboembolism (VTE) in Europe. The number of VTE events and associated morbidity and mortality" *Thromb. Haemost.* 2007; 98(4):756-64.
Curran et al., "Metabolic engineering of muconic acid production in *Saccharomyces cerevisiae*" Metab. Eng., 2013; 15:55-66. Epub Nov. 17, 2012.
Dahl et al., "Engineering dynamic pathway regulation using stress-response promoters" Nat. Biotechnol., 2013; 31:1039-46. Epub Oct. 20, 2013.
Dhamankar et al. "Microbial chemical factories: recent advances in pathway engineering for synthesis of value added chemicals" *Curr. Opin. Struct. Biol.* Aug. 2011; 21(4):488-94.
Draths et al., "Environmentally Compatible Synthesis of Adipic Acid from D-Glucose" J. Am. Chem. Soc., 1994; 116(1):399-400.
Fisher et al., "Enhancing Tolerance to Short-Chain Alcohols by Engineering the *Escherichia coli* AcrB Efflux Pump to Secrete the Non-native Substrate n-Butanol" ACS Synth. Biol., 2014; 3(1):30-40. Epub Aug. 30, 2013.
Fuchs et al., "Microbial degradation of aromatic compounds—from one strategy to four" Nat. Rev. Microbiol., 2011; 9(11):803-16.
Gaille et al. "Salicylate biosynthesis in *Pseudomonas aeruginosa*. Purification and characterization of PchB, a novel bifunctional enzyme displaying isochorismate pyruvate-lyase and chorismate mutase activities" *J. Biol. Chem.* 2002; 277(24):21768-75.

(Continued)

*Primary Examiner* — Suzanne M Noakes
(74) *Attorney, Agent, or Firm* — Mueting, Raasch & Gebhardt, P.A.

(57) ABSTRACT

The invention provides a recombinant microorganism that has been genetically engineered to contain metabolic pathway for the production of muconic acid from a salicylic acid intermediate. The genetically engineered metabolic pathway comprises both biosynthetic and biodegradative elements.

10 Claims, 9 Drawing Sheets

(56) References Cited

OTHER PUBLICATIONS

Gaille et al., "Isochorismate synthase (PchA), the first and rate-limiting enzyme in salicylate biosynthesis of Pseudomonas aeruginosa" J. Biol. Chem., 2003; 278:16893-8.
Gao et al. "Clean and Convenient One-Pot Synthesis of 4-Hydroxycoumarin and 4-Hydroxy-2-Quinolinone Derivatives" Synthetic Commun. 2010; 40:732-8.
Geissler et al., "Purification and properties of benzoate-coenzyme A ligase, a Rhodopseudomonas palustris enzyme involved in the anaerobic degradation of benzoate" J. Bacteriol. 1988;170(4):1709-14.
Gerhardt et al. (eds.) Methods for General and Molecular Bacteriology, American Society for Microbiology, 1994; Cover page, publisher's page, and chapters 13-14 and 16-18.
Gibson et al. "Enzymatic assembly of DNA molecules up to several hundred kilobases" Nat. Methods, 2009; 6(5):343-5.
Hammer et al., "Synthetic promoter libraries—tuning of gene expression" Trends Biotechnol, Feb. 2006; 24:53-5.
Heeb et al. "Quinolones: from antibiotics to autoinducers" FEMS Microbiol. Rev. 2011; 35(2):247-74.
Heit et al., "Estimated annual number of incident and recurrent, non-fatal and fatal venous thromboembolism (VTE) events in the US" Blood, 2005; 106:267a-267a.
Huang et al., "Caffeic acid production enhancement by engineering a phenylalanine over-producing Escherichia coli strain," Dec. 2013 Biotechnol. Bioeng. 110:3188-3196. Available online on Jul. 11, 2013.
Ishiyama et al., "Novel pathway of salicylate degradation by Streptomyces sp. strain WA46" Appl. Environ. Microbiol. 2004; 70(3):1297-306.
Ivanov et al. "New Efficient Catalysts in the Synthesis of Warfarin and Acenocoumarol" Arch. Pharm. (Weinheim) 1990; 323(8):521-2.
Juminaga et al., "Modular engineering of L-tyrosine production in Escherichia coli" Appl. Environ. Microbiol., 2012; 78(1):89-98.
Kai et al. "Scopoletin is biosynthesized via ortho-hydroxylation of feruloyl CoA by a 2-oxoglutarate-dependent dioxygenase in Arabidopsis thaliana" Plant J. 2008; 55(6):989-9.
Kikuchi et al. "Mutational analysis of the feedback sites of phenylalanine-sensitive 3-deoxy-D-arabino-heptulosonate-7-phosphate synthase of Escherichia coli" Appl. Environ. Microbiol. 1997; 63(2):761-2.
Leonard et al. "Engineering central metabolic pathways for high-level flavonoid production in Escherichia coli" Appl. Environ. Microbiol. 2007; 73(12):3877-86.
Lequesne et al., "The Natural Coumarins—Occurrence, Chemistry and Biochemistry" J. Am. Chem. Soc. 1983; 105:6536.
Lim et al. "High-Yield Resveratrol Production in Engineered Escherichia coli" Appl. Environ. Microbiol. 2011; 77(10):3451-60.
Lin et al. "Biosynthesis of caffeic acid in Escherichia coli using its endogenous hydroxylase complex" Microb. Cell. Fact. Apr. 4, 2012; 11:42, 9 pages.
Lin et al, "Microbial Biosynthesis of the Anticoagulant Precursor 4-Hydroxycoumarin", Nature Communications, Oct. 16, 2013, 8 pages.
Lin et al., "Combinatorial biosynthesis of plant-specific coumarins in bacteria" Metab. Eng., 2013; 18:69-77. Epub Apr. 30, 2013.
Lin et al. "Extending shikimate pathway for the production of muconic acid and its precursor salicylic acid in Escherichia coli" Metab. Eng., 2014; 23:62-69. Epub Feb. 25, 2014.
Lin, "Production of Muconic Acid and Its Precursor Salicylic Acid by Extending the E. coli Shikimate Pathway," 14AIChE Annual Meeting, Nov. 16-21, 2014. Abstract No. 386770, 14AIChE Annual Meeting, Atlanta, Georgia, Nov. 19, 2014, [retrieved on Apr. 20, 2015], 1 pg. Retrieved from the Internet: <URL:aiche.confex.com/aiche/2014/webprogram/Paper386770 >.
Ling, et al., "Enediyne antitumor antibiotic maduropeptin biosynthesis featuring a C-methyltransferase that acts on a CoA-tethered aromatic substrate" J. Am. Chem. Soc. 2010; 132(36):12534-6.
Liu et al. "A novel 4-hydroxycoumarin biosynthetic pathway" Plant Mol. Biol. 2010; 72(1-2):17-25.

Lütke-Eversloh et al. "L-tyrosine production by deregulated strains of Escherichia coli" Appl. Microbiol. Biotechnol. 2007; 75(1):103-10.
Lütke-Eversloh et al. "Combinatorial pathway analysis for improved L-tyrosine production in Escherichia coli: Identification of enzymatic bottlenecks by systematic gene overexpression" Metab. Eng. 2008; 10(2):69-77.
Martin et al., "Engineering a mevalonate pathway in Escherichia coli for production of terpenoids" Nat. Biotechnol. 2003; 21(7):796-802.
Matsumoto et al. "Molecular cloning and functional analysis of the ortho-hydroxylases of p-coumaroyl coenzyme A/feruloyl coenzyme A involved in formation of umbelliferone and scopoletin in sweet potato, Ipomoea batatas (L.) Lam." Phytochemistry, Feb. 2012; 74:49-57.
Melnikova, "The anticoagulants market" Nat. Rev. Drug Discov. 2009; 8(5):353-4.
Murray et al., Natural Coumarins: occurrence, chemistry and biochemistry, John Wiley & Sons Ltd., Chichester, New York; 1982. Cover page, title page and table of contents.
Nagachar et al. "Roles of trpE2, entC and entD in salicylic acid biosynthesis in Mycobacterium smegmatis" FEMS Microbiol. Lett. 2010; 308(2):159-65.
Nakagawa et al. "A bacterial platform for fermentative production of plant alkaloids" Nat. Commun. 2011; 2:326. 8 pages.
Niu et al., "Benzene-free synthesis of adipic acid" Biotechnol. Prog., Mar.-Apr. 2002; 18(2):201-11.
Oliver et al., "Cyanobacterial conversion of carbon dioxide to 2,3-butanediol" Proc. Natl. Acad. Sci. U. S. A., 2013; 110:1249-54. Epub Jan. 7, 2013.
Patnaik et al., "L-tyrosine production by recombinant Escherichia coli: fermentation optimization and recovery" Biotechnol. Bioeng., Mar. 1, 2008; 99(4):741-52.
Payne et al. "Synthesis and evaluation of 2,5-dihydrochorismate analogues as inhibitors of the chorismate-utilising enzymes" Org. Biomol. Chem. 2009; 7(11):2421-9.
Pickens et al., "Biochemical analysis of the biosynthetic pathway of an anticancer tetracycline SF2575" J. Am. Chem. Soc. 2009; 131(48):17677-89.
Rabinovitch-Deere et al., "Synthetic biology and metabolic engineering approaches to produce biofuels" Chem. Rev., 2013; 113(7):4611-32. Epub Mar. 15, 2013.
Ro et al. "Production of the antimalarial drug precursor artemisinic acid in engineered yeast" Nature, 2006; 440(7086):940-3.
Rogozinska et al. "Efficient "on water" organocatalytic protocol for the synthesis of optically pure warfarin anticoagulant" Green Chem. 2011; 13:1155-7.
Rueping et al. "A review of new developments in the Friedel-Crafts alkylation—From green chemistry to asymmetric catalysis" Beilstein J. Org. Chem. 2010; 6:6. 24 pages.
Salis et al. "Automated design of synthetic ribosome binding sites to control protein expression" Nat. Biotechnol. 2009; 27(10): 946-50.
Sambrook et al., Molecular cloning: a laboratory manual, $2^{nd}$ ed. Cold Spring Harbor Laboratory Press: Cold Spring Harbor, New York; 1989. Cover page, title page, and table of contents. 30 pgs.
Santos et al. "Optimization of a heterologous pathway for the production of flavonoids from glucose" Metab. Eng. 2011; 13(4):392-400.
Seo, J. S., Keum, Y. S., Li, Q. X., 2009. Bacterial degradation of aromatic compounds. Int. J. Environ. Res. Public. Health. 6, 278-309.
Shen et al. "Metabolic engineering of Escherichia coli for 1-butanol and 1-propanol production via the keto-acid pathways" Metab. Eng, 2008; 10:312-20.
Shen et al., "Driving forces enable high-titer anaerobic 1-butanol synthesis in Escherichia coli" Appl. Environ. Microbial. 2011; 77(9):2905-15.
Shen et al., "Inhibition of acetate accumulation leads to enhanced production of (R,R)-2,3-butanediol from glycerol in Escherichia coli" J Ind Microbiol Biotechnol, Nov. 2012; 39(11):1725-9.

(56) References Cited

OTHER PUBLICATIONS

Smolke et al., "Controlling the metabolic flux through the carotenoid pathway using directed mRNA processing and stabilization" Metab. Eng., Oct. 2001; 3(4):313-21.

Sun, X., Lin, Y., Huang, Q., Yuan, Q., Yan, Y., Apr. 2013. A novel muconic acid biosynthesis approach by shunting tryptophan biosynthesis via anthranilate. Appl. Environ. Microbiol. 79, 4024-30. Epub Apr. 19, 2013.

Transparency Market Research "Salicylic Acid Market for Pharmaceutical, Skin care, Hair care and Other Applications-Global Industry Analysis, Size, Share, Growth, Trends, and Forecast 2013-2019" Sep. 26, 2013; Description and Table of Contents, [retrieved on Apr. 19, 2016] <transparencymarketresearch.com/salicylic-acid>; 10 pages.

Vialart et al. "A 2-oxoglutarate-dependent dioxygenase from *Ruta graveolens* L. exhibits *p*-coumaroyl CoA 2'-hydroxylase activity (C2'H): a missing step in the synthesis of umbelliferone in plants" *Plant J.* May 2012; 70(3):460-70.

Weber et al., "Biosynthesis of cis,cis-muconic acid and its aromatic precursors, catechol and protocatechuic acid, from renewable feedstocks by *Saccharomyces cerevisiae*" Appl. Environ. Microbiol, 2012; 78:8421-30.

Xu et al., "Engineering plant metabolism into microbes: from systems biology to synthetic biology" Curr. Opin. Biotechnol., Apr. 2013; 24(2):291-9. Epub Sep. 15, 2012.

Xu et al. "Modular optimization of multi-gene pathways for fatty acids production in *E. coli.*" *Nat. Commun.* 2013; 4:1409.

Yan et al. "High-yield anthocyanin biosynthesis in engineered *Escherichia coli*" *Biotechnol. Bioeng.* 2008; 100(1):126-40.

Zha et al. "Improving cellular malonyl-CoA level in *Escherichia coli* via metabolic engineering" *Metab. Eng.* 2009; 11(3):192-8.

Zhang et al., "Expanding metabolism for biosynthesis of nonnatural alcohols" Proc. Natl. Acad. Sci. U.S.A., 2008; 105:20653-8.

Zhang et al., "PqsD is responsible for the synthesis of 2,4-dihydroxyquinoline, an extracellular metabolite produced by *Pseudomonas aeruginosa*" *J. Biol. Chem.* 2008; 283(43):28788-94.

Zhang et al. "A synthetic metabolic pathway for production of the platform chemical isobutyric acid" ChemSusChem, Aug. 22, 2011; 4(8):1068-70.

Zhang et al. "Design of a dynamic sensor-regulator system for production of chemicals and fuels derived from fatty acids" *Nat. Biotechnol.* Mar. 25, 2012; 30(4):354-9.

\* cited by examiner

FIG. 5

(A) EntC from *E. coli* (SEQ ID NO:1)

MDTSLAEEVQQTMATLAPNRFFFMSPYRSFTTSGCFARFDEPAVNGDSPDSPFQQKLAA
LFADAKAQGIKNPVMVGAIPFDPRQPSSLYIPESWQSFSRQEKQASARRFTRSQSLNVV
ERQAIPEQTTFEQMVARAAALTATPQVDKVVLSRLIDITTDAAIDSGVLLERLIAQNPV
SYNFHVPLADGGVLLGASPELLLRKDGERFSSIPLAGSARRQPDEVLDREAGNRLLASE
KDRHEHELVTQAMKEVLRERSSELHVPSSPQLITTPTLWHLATPFEGKANSQENALTLA
CLLHPTPALSGFPHQAATQVIAELEPFDRELFGGIVGWCDSEGNGEWVVTIRCAKLREN
QVRLFAGAGIVPASSPLGEWRETGVKLSTMLNVFGLH

(B) PchB from *P. fluorescence* (SEQ ID NO:2)

MLAFDPMNFPLVDPDMKTPEQCSGLDDVRCGIDAMDQQIIQALGRRLAYVKAAAQFKPT
EDSIAAPERVAAMLPQRRQWAEQASLDPMFVVPLFAQIIHWNIAQQVRHWRRQHGLDQG
AQDE

(C) NahG from *E. coli* (SEQ ID NO:3)

MQNSTSALNVSIIGGGIAGVALALDLCRHAHLNVQLFEAAPAFGEVGAGVSFGANAVRA
IAGLGIAEPYGKIADSNPAPWQDIWFEWRNGRDAKYLGCSVAEGVGQSSVHRADFLDAL
ASQLPDGIAQFGKRAQRVEQDGEQVRVTFTDGSEHRCDLLIGADGIKSSIRDHVLQGLN
QPLASPRFSGTCAYRGLIDSQQLREAYRARGVDEHLIDVPQMYLGLDGHILTFPVKQGR
LINVVAFISDRSQPNPVWPSDTPWVRNATQAEMLAAFEGWDDAAQVLLECIPTPSLWAL
HDLAELPGYVHGRVGLIGDAAHAMLPHQGAGAGQGLEDAWLLARLLEDPKVLDKRPQAV
LDAYDAVRRPRACRVQRTSFEAGELYEFRDPAVLADEERLGKVLAERFDWLWNHDMQED
LLQARELLGLRAQAA

(D) CatA from *P. putida* (SEQ ID NO:4)

MTVKISHTADIQAFFNRVAGLDHAEGNPRFKQIILRVLQDTARLIEDLEITEDEFWHAV
DYLNRLGGRNEAGLLAAGLGIEHFLDLLQDAKDAEAGLGGGTPRTIEGPLYVAGAPLAQ
GEARMDDGTDPGVVMFLQGQVFDADGKPLAGATVDLWHANTQGTYSYFDSTQSEFNLRR
RIITDAEGRYRARSIVPSGYGCDPQGPTQECLDLLGRHGQRPAHVHFFISAPGHRHLTT
QINFAGDKYLWDDFAYATRDGLIGELRFVEDAAAARDRGVQGERFAELSFDFRLQGAKS
PDAEARSHRPRALQEG

FIG. 5

(E) codon-optimized *nahG* from *E. coli* (SEQ ID NO:5)

ATGCAGAACAGTACCAGCGCCCTGAACGTTAGCATCATTGGCGGCGGTATCGCAGGCGT
TGCACTGGCCCTGGACTTATGTCGCCACGCCCACCTGAACGTGCAGCTGTTCGAGGCAG
CCCCGGCCTTTGGCGAAGTTGGTGCCGGTGTTAGCTTCGGCGCCAATGCAGTGCGTGCA
ATCGCCGGTCTGGGTATCGCAGAGCCGTACGGCAAAATTGCCGACAGTAATCCGGCCCC
GTGGCAGGACATCTGGTTCGAATGGCGCAATGGCCGTGATGCCAAATACCTGGGTTGCA
GCGTTGCCGAAGGCGTTGGTCAAAGCAGTGTGCACCGTGCCGATTTCCTGGACGCTCTG
GCTTCTCAGCTGCCGGACGGTATCGCTCAGTTCGGTAAACGTGCTCAGCGTGTTGAACA
GGACGGTGAGCAAGTGCGTGTGACATTCACAGACGGCAGCGAGCACCGCTGCGATCTGC
TGATTGGTGCCGACGGTATCAAGAGTAGCATCCGTGACCACGTGTTACAGGGCCTGAAT
CAACCGCTGGCAAGCCCGCGTTTTAGCGGCACCTGCGCCTATCGCGGTCTGATCGATAG
CCAGCAGCTGCGTGAGGCCTATCGTGCCCGTGGCGTGGACGAGCATCTGATTGACGTGC
CGCAGATGTACCTGGGCCTGGACGGCCACATCCTGACCTTCCCGGTTAAACAAGGCCGC
CTGATCAACGTGGTGGCCTTCATCAGTGACCGCAGCCAACCGAACCCGGTTTGGCCGAG
CGATACACCGTGGGTTCGTAATGCCACCCAAGCCGAGATGCTGGCCGCATTCGAGGGCT
GGGATGATGCAGCCCAAGTGCTGCTGGAGTGCATCCCGACCCCTAGTCTGTGGGCCCTG
CACGACCTGGCAGAATTACCGGGCTACGTTCACGGCCGTGTTGGCTTAATCGGCGACGC
CGCCCACGCAATGTTACCGCATCAGGGTGCCGGTGCAGGTCAGGGTCTGGAGGATGCCT
GGTTACTGGCCCGCCTGCTGGAAGACCCGAAGGTGCTGGACAAACGCCCGCAGGCAGTG
CTGGATGCCTATGACGCCGTTCGTCGTCCTCGTGCCTGCCGTGTGCAGCGTACCAGCTT
CGAGGCCGGCGAACTGTATGAGTTCCGTGACCCGGCCGTGTTAGCCGACGAGGAGCGTC
TGGGCAAAGTTCTGGCCGAACGCTTTGACTGGCTGTGGAACCACGACATGCAGGAAGAC
TTATTACAGGCCCGTGAGCTGCTGGGTTTACGTGCCCAAGCCGCCTAA

FIG. 5

(F) catA from *E. coli* (SEQ ID NO:6)

ATGACCGTGAAAATTTCCCACACTGCCGACATTCAAGCCTTCTTCAACCGGGTAGCTGG
CCTGGACCATGCCGAAGGAAACCCGCGCTTCAAGCAGATCATTCTGCGCGTGCTGCAAG
ACACCGCCCGCCTGATCGAAGACCTGGAGATTACCGAGGACGAGTTCTGGCACGCCGTC
GACTACCTCAACCGCCTGGGCGGCCGTAACGAGGCAGGCCTGCTGGCTGCTGGCCTGGG
TATCGAGCACTTCCTCGACCTGCTGCAGGATGCCAAGGATGCCGAAGCCGGCCTTGGCG
GCGGCACCCCGCGCACCATCGAAGGCCGTTGTACGTTGCCGGGGCGCCGCTGGCCCAG
GGCGAAGCGCGCATGGACGACGGCACTGACCCAGGCGTGGTGATGTTCCTTCAGGGCCA
GGTGTTCGATGCCGACGGCAAGCCGTTGGCCGGTGCCACCGTCGACCTGTGGCACGCCA
ATACCCAGGGCACCTATTCGTACTTCGATTCGACCCAGTCCGAGTTCAACCTGCGTCGG
CGTATCATCACCGATGCCGAGGGCCGCTACCGCGCGCTCGATCGTGCCGTCCGGGTA
TGGCTGCGACCCGCAGGGCCCAACCCAGGAATGCCTGGACCTGCTCGGCCGCCACGGCC
AGCGCCCGGCGCACGTGCACTTCTTCATCTCGGCACCGGGGCACCGCCACCTGACCACG
CAGATCAACTTTGCTGGCGACAAGTACCTGTGGGACGACTTTGCCTATGCCACCCGCGA
CGGGCTGATCGGCGAACTGCGTTTTGTCGAGGATGCGGCGGCGGCGCGCGACCGCGGTG
TGCAAGGCGAGCGCTTTGCCGAGCTGTCATTCGACTTCCGCTTGCAGGGTGCCAAGTCG
CCTGACGCCGAGGCGCGAAGCCATCGGCCGCGGGCGTTGCAGGAGGGCTGA

(G) AroL from *E. coli* (SEQ ID NO:7)

MTQPLFLIGPRGCGKTTVGMALADSLNRRFVDTDQWLQSQLNMTVAEIVEREEWAGFRA
RETAALEAVTAPSTVIATGGGIILTEFNRHFMQNNGIVVYLCAPVSVLVNRLQAAPEED
LRPTLTGKPLSEEVQEVLEERDALYREVAHIIIDATNEPSQVISEIRSALAQTINC

(H) PpsA from *E. coli* (SEQ ID NO:8)

MSNNGSSPLVLWYNQLGMNDVDRVGGKNASLGEMITNLSGMGVSVPNGFATTADAFNQF
LDQSGVNQRIYELLDKTDIDDVTQLAKAGAQIRQWIIDTPFQPELENAIREAYAQLSAD
DENASFAVRSSATAEDMPDASFAGQQETFLNVQGFDAVLVAVKHVFASLFNDRAISYRV
HQGYDHRGVALSAGVQRMVRSDLASSGVMFSIDTESGFDQVVFITSAWGLGEMVVQGAV
NPDEFYVHKPTLAANRPAIVRRTMGSKKIRMVYAPTQEHGKQVKIEDVPQEQRDIFSLT
NEEVQELAKQAVQIEKHYGRPMDIEWAKDGHTGKLFIVQARPETVRSRGQVMERYTLHS
QGKIIAEGRAIGHRIGAGPVKVIHDISEMNRIEPGDVLVTDMTDPDWEPIMKKASAIVT
NRGGRTCHAAIIARELGIPAVVGCGDATERMKDGENVTVSCAEGDTGYVYAELLEFSVK
SSSVETMPDLPLKVMMNVGNPDRAFDFACLPNEGVGLARLEFIINRMIGVHPRALLEFD
DQEPQLQNEIREMMKGFDSPREFYVGRLTEGIATLGAAFYPKRVIVRLSDFKSNEYANL
VGGERYEPDEENPMLGFRGAGRYVSDSFRDCFALECEAVKRVRNDMGLTNVEIMIPFVR
TVDQAKAVEELARQGLKRGENGLKIIMMCEIPSNALLAEQFLEYFDGFSIGSNDMTQL
ALGLDRDSGVVSELFDERNDAVKALLSMAIRAAKKQGKYVGICGQGPSDHEDFAAWLME
EGIDSLSLNPDTVVQTWLSLAELKK

FIG. 5

(I) TktA of from *E. coli* (SEQ ID NO:9)

MSSRKELANAIRALSMDAVQKAKSGHPGAPMGMADIAEVLWRDFLKHNPQNPSWADRDR
FVLSNGHGSMLIYSLLHLTGYDLPMEELKNFRQLHSKTPGHPEVGYTAGVETTTGPLGQ
GIANAVGMAIAEKTLAAQFNRPGHDIVDHYTYAFMGDGCMMEGISHEVCSLAGTLKLGK
LIAFYDDNGISIDGHVEGWFTDDTAMRFEAYGWHVIRDIDGHDAASIKRAVEEARAVTD
KPSLLMCKTIIGFGSPNKAGTHDSHGAPLGDAEIALTREQLGWKYAPFEIPSEIYAQWD
AKEAGQAKESAWNEKFAAYAKAYPQEAAEFTRRMKGEMPSDFDAKAKEFIAKLQANPAK
IASRKASQNAIEAFGPLLPEFLGGSADLAPSNLTLWSGSKAINEDAAGNYIHYGVREFG
MTAIANGISLHGGFLPYTSTFLMFVEYARNAVRMAALMKQRQVMVYTHDSIGLGEDGPT
HQPVEQVASLRVTPNMSTWRPCDQVESAVAWKYGVERQDGPTALILSRQNLAQQERTEE
QLANIARGGYVLKDCAGQPELIFIATGSEVELAVAAYEKLTAEGVKARVVSMPSTDAFD
KQDAAYRESVLPKAVTARVAVEAGIADYWYKYVGLNGAIVGMTTFGESAPAELLFEEFG
FTVDNVVAKAKELL

(J) feedback-inhibition-resistant AroG from *E. coli* (SEQ ID NO:10)

MNYQNDDLRIKEIKELLPPVALLEKFPATENAANTVAHARKAIHKILKGNDDRLLVVIG
PCSIHDPVAAKEYATRLLALREELKDELEIVMRVYFEKPRTTVGWKGLINDPHMDNSFQ
INDGLRIARKLLLDINDSGLPAAGEFLDMITPQYLADLMSWGAIGARTTESQVHRELAS
GLSCPVGFKNGTDGTIKVAIDAINAAGAPHCFLSVTKWGHSAIVNTSGNGDCHIILRGG
KEPNYSAKHVAEVKEGLNKAGLPAQVMIDFSHANSSKQFKKQMDVCADVCQQIAGGEKA
IIGVMVESHLVEGNQSLESGEPLAYGKSITDACIGWEDTDALLRQLANAVKARRG

MICROBIAL PRODUCTION OF MUCONIC ACID AND SALICYLIC ACID

This application claims the benefit of U.S. Provisional Application Ser. No. 61/939,593, filed Feb. 13, 2014, which is incorporated by reference herein.

SEQUENCE LISTING

This application contains a Sequence Listing electronically submitted to the United States Patent and Trademark Office via EFS-Web as an ASCII text file entitled "235-02380101_SequenceListing_ST25.txt" having a size of 31 kilobytes and created on Feb. 12, 2015. The information contained in the Sequence Listing is incorporated by reference herein.

BACKGROUND

Fossil fuels supply the world with not only energy but also important feedstocks for chemical industry. However, the shrinking availability of fossil reserves and the deteriorating environment compel people to explore renewable alternatives for the production of fuels, chemicals, and pharmaceuticals. Fortunately, the metabolic diversity of biological systems provides us with an extremely rich chemical repertoire. In recent years, the development of metabolic engineering has enabled the establishment of microbial chemical factories by constituting heterologous or non-natural biosynthetic pathways into genetically advantageous microbial hosts (Ajikumar et al., 2010 Science 330:70-4; Anthony et al., 2009 Metab. Eng. 11:13-9; Atsumi et al., 2008 Metab. Eng. 10:305-11; Huang et al., 2013 Biotechnol. Bioeng. 110:3188-96; Lin et al., 2013b Metab. Eng. 18:69-77; Lin et al., 2012 Microb. Cell Fact. 11:42; Shen et al., 2008 Metab. Eng. 10:312-20; Shen et al., 2012 J. Ind. Microbiol. Biotechnol. 39:1725-9; Zhang et al., 2008 Proc. Natl. Acad. Sci. U.S.A. 105:20653-8).

Muconic acid (MA) is a platform chemical that serves as the precursor to several bio-plastics. It is also a naturally-occurring metabolite. Muconic acid is present in biological systems as an intermediate in the microbial degradation of aromatic hydrocarbons (Fuchs et al., 2011 Nat. Rev. Microbiol. 9:803-16). In past 20 years, many efforts have been made for the microbial production of muconic acid. Draths and Frost reported the earliest study on the artificial biosynthesis of muconic acid in Escherichia coli from renewable carbon source glucose (Draths et al., 1994 J. Am. Chem. Soc. 116:399-400). By introducing three heterologous enzymes 3-dehydroshikimate dehydratase, protocatechuic acid decarboxylase and catechol 1,2-dioxygenase (CDO), the carbon flux was redirected from the E. coli native shikimate pathway to the biosynthesis of muconic acid. Metabolically optimized strains carrying this artificial pathway were able to produce up to 2.4 g/L of muconic acid via two-stage bioconversion in shake flasks (Draths et al., 1994 J. Am. Chem. Soc. 116:399-400) and 38.6 g/L via fed-batch fermentation (Niu et al., 2002 Biotechnol. Prog. 18:201-11). Afterwards, the same pathway was reconstituted in Saccharomyces cerevisiae (Weber et al., 2012 Appl. Environ. Microbiol. 78:8421-30), and the highest titer reported was nearly 141 mg/L (Curran et al., 2013 Metab. Eng. 15:55-66).

Muconic acid is easily converted into adipic acid by chemical hydrogenation, and adipic acid is a direct building block for nylon-6,6 and polyurethane (Sun et al., 2013 Appl. Environ. Microbiol. 79:4024-30). In addition, muconic acid is a synthetic precursor to terephthalic acid, a chemical used for manufacturing polyethylene terephthalate (PET) and polyester (Curran et al., 2013 Metab. Eng. 15:55-66). The global production of adipic acid and terephthalic acid is 2.8 and 71 million metric tons, respectively (Curran et al., 2013 Metab. Eng. 15:55-66).

Salicylic acid (SA) is an important drug precursor mainly used for producing pharmaceuticals such as aspirin and lamivudine (an anti-HIV drug). Like muconic acid, it is a naturally-occurring metabolite. In biological systems, salicylic acid serves not only as a plant hormone (Chen et al., 2009 Plant Signal Behav. 4:493-6) but also as a biosynthetic precursor of bacterial siderophore (Gaille et al., 2002 J. Biol. Chem. 277:21768-75). Salicylic acid esters and salts used in sunscreens and medicaments account for another large portion of salicylic acid consumption. The global market for salicylic acid products was estimated to be $292.5 million in 2012 and is expected to reach $521.2 million in 2019, growing at an annual increase of 8.6% ("Salicylic Acid Market for Pharmaceutical, Skin care, Hair care and Other Applications-Global Industry Analysis, Size, Share, Growth, Trends, and Forecast 2013-2019," 2013 Transparency Market Research).

Muconic acid and salicylic acid are thus naturally-occurring organic acids having great commercial value. Muconic acid is a potential platform chemical for the manufacture of several widely-used consumer plastics; while salicylic acid is mainly used for producing pharmaceuticals, skincare and haircare products. At present, commercial production of muconic acid, salicylic acid, adipic acid, and terephthalic acid predominantly relies on organic chemical synthesis using petroleum-derived chemicals, such as benzene, as starting materials. These chemical synthesis processes are considered nonrenewable and environmentally unfriendly. Therefore, it is of great importance to develop "green" synthetic approaches that can utilize renewable feedstocks.

SUMMARY OF THE INVENTION

The present invention involves the construction of a biosynthetic pathway for muconic acid and salicylic acid production using recombinant microorganisms such as E. coli. Muconic acid and salicylic acid are high-value commodity chemicals. Producing high-value chemicals through microbial conversion is an attractive alternative to the current petroleum-based chemical industry.

A novel pathway for muconic acid and salicylic acid production is described and validated. The novel biosynthetic pathway involves a plurality of enzymatic modules and is exemplified in the figures and examples included herewith. The biosynthetic pathway can be introduced into any commercially useful microorganism, such as E. coli. Advantageously, the resulting metabolically engineered microorganism can be employed in large scale fermentations to produce muconic acid, salicylic acid, or other metabolites in the engineered pathway that are of interest. Muconic acid, salicylic acid, or their metabolites can be isolated and further derivatized chemically or enzymatically to yield a large array of additional commercially important products such as adipic acid and terephthalic acid, which in turn can be incorporated into other materials including bio-based polymers such as polyethylene terephthalate (PET) and polyester.

The present invention provides cells, for example microbial cells, also referred to herein as microorganisms, which are genetically engineered for the production of muconic acid from a salicylic acid intermediate, as well as methods for making the genetically engineered cells and methods for producing and isolating salicylic acid, muconic acid, and/or their derivatives and downstream metabolites, from the cells or cell culture.

In one aspect, the invention provides a genetically engineered cell having a genetically engineered metabolic pathway for the production of muconic acid from a salicylic acid intermediate. The genetically engineered cell is preferably a microbial cell, i.e., a microorganism. The genetically engineered metabolic pathway can include at least one enzyme associated with the biosynthesis of salicylic acid, and at least one enzyme associated with the conversion of salicylic acid to muconic acid. In some embodiments, the enzyme associated with the biosynthesis of salicylic acid includes one or both of an isochorismate synthase (ICS) and an isochorismate pyruvate lyase (IPL). The enzymes associated with the biosynthesis of salicylic acid can be introduced into the host cell using a "synthetic" enzymatic module. In some embodiments, the enzyme associated with the conversion of salicylic acid to muconic acid includes one or both of a salicylate 1-monooxygenase (SMO) and a catechol 1,2-dioxygenase (CDO). The enzymes associated with the conversion of salicylic acid to muconic acid can be introduced into the host cell using a "degradative" enzymatic module. In an exemplary embodiment, a genetically engineered microorganism includes a first module (i.e., a synthetic enzymatic module) expressing an isochorismate synthase (ICS) and an isochorismate pyruvate lyase (IPL), and a second module (i.e., a degradative enzymatic module) expressing a salicylate 1-monooxygenase (SMO) and a catechol 1,2-dioxygenase (CDO). The first and second modules may be present on different plasmids, or they can be present on the same plasmid.

The genetically engineered metabolic pathway optionally further includes at least one enzyme associated with enhanced chorismate availability. In some embodiments, the enzyme or enzymes associated with enhanced chorismate availability include enzymes that increase carbon flow toward chorismate. An enzyme or enzymes associated with enhanced chorismate availability can be introduced into the host cell using a "precursor enhancing" enzymatic module. In an exemplary embodiment, a genetically engineered microorganism optionally includes a third module (i.e., a precursor enhancing enzymatic module) expressing one or more enzymes encoded by aroL, ppsA, tktA, and/or aroG$^{fbr}$. The third module may be present on a plasmid. In exemplary embodiments, the first and third modules are present on the same or different high copy number plasmid(s), and the second module is present on a low copy number plasmid.

The genetically engineered biosynthetic pathway can include one or more enzymes that are heterologous to the host cell, and/or it can include one or more enzymes that are naturally occurring in the host cell. In the case of an enzyme naturally occurring in the host cell, the enzyme can be expressed at naturally occurring levels, or it can be overexpressed as a component of the genetically engineered pathway.

In some aspects, the genetically engineered microorganism of the invention has been further engineered to overproduce at least one aromatic amino acid, such as phenylalanine or tyrosine. The genetically engineered microorganism of the invention may be further engineered to knock out one or more enzymes involved in biosynthesis of an aromatic amino acid. Exemplary enzymes encoding an aromatic amino acid include pheA, tyrA and trpD. In some embodiments, pheA and tyrA are knocked out, and trpD, if present, is not disrupted.

The genetically engineered microorganism of the invention is preferably a bacterium or a yeast. In some embodiments, the genetically engineered microorganism is selected from *Escherichia coli*, *Bacillus subtilis* *Bacillus licheniformis*, *Alcaligenes eutrophus*, *Rhodococcus erythropolis*, *Paenibacillus macerans*, *Pseudomonas putida*, *Enterococcus faecium*, *Saccharomyces cerevisiae*, *Lactobacillus plantarum*, *Enterococcus gallinarium* and *Enterococcus faecalis*. An exemplary genetically engineered microorganism is *E. coli*.

In exemplary embodiments, the genetically engineered microorganism includes at least one plasmid selected from the group consisting of pCS-EP, pZE-EP, pSA-EP, pCS-NC, pZE-NC, pSA-NC, pCS-APTA, pZE-EP-APTA.

The invention also provides a method for using the genetically engineered host cell, for example the genetically engineered microorganism, to produce a downstream metabolite of chorismate, preferably an organic acid such as salicylic acid or muconic acid. The genetically engineered cell is cultured under conditions to produce the organic acid, and the organic is optionally separated from the genetically engineered cell. Optionally, the organic acid is isolated and/or purified.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 5 shows exemplary polynucleotides sequences and exemplary amino acid sequences for use in the invention. (A) Amino acid sequence of EntC from *E. coli* (SEQ ID NO:1). (B) Amino acid sequence of PchB from *P. fluorescence* (SEQ ID NO:2). (C) Amino acid sequence of NahG from *E. coli* (SEQ ID NO:3). (D) Amino acid sequence of CatA from *P. putida* (SEQ ID NO:4). (E) Polynucleotide sequence of codon-optimized nahG from *E. coli* (SEQ ID NO:5). (F) Polynucleotide sequence of catA from *E. coli* (SEQ ID NO:6). (G) Amino acid sequence of AroL from *E. coli* (SEQ ID NO:7). (H) Amino acid sequence of PpsA from *E. coli* (SEQ ID NO:8). (I) Amino acid sequence TktA of from *E. coli* (SEQ ID NO:9). (J) Amino acid sequence of feedback-inhibition-resistant AroG from *E. coli* (SEQ ID NO:10).

DETAILED DESCRIPTION OF ILLUSTRATIVE EMBODIMENTS

The present invention provides a genetically engineered microorganism (also referred to herein as a genetically engineered microbe) containing a biosynthetic pathway resulting in production of muconic acid (MA) from chorismate, via a salicylic acid (SA) intermediate. Also provided by the invention are methods of making the genetically engineered organism, and methods of using the genetically engineered organism, for example to produce muconic acid, salicylic acid, or other metabolites.

This novel biosynthetic pathway is a de novo muconic acid biosynthetic pathway that extends the shikimate pathway by combining a salicylic acid biosynthetic pathway (via a first "synthetic" enzymatic module), with a partial salicylic acid degradation pathway (via a second "degradative" enzymatic module), thereby creatively bridging SA biosynthesis with its partial degradation pathway. Efficient production of MA was surprising because biosynthesis and degradation of a specific molecule (in this case, salicylic acid) typically do not occur simultaneously in natural settings. The resulting biosynthetic pathway thus quite unexpectedly yielded an efficient microbial platform for the production of muconic and other compounds for which muconic is a precursor.

The biosynthetic pathway optionally includes a third "precursor enhancing" enzymatic module designed to increase the availability of chorismate, which is the precursor for salicylic acid synthesis via the synthetic module.

Figure 1:
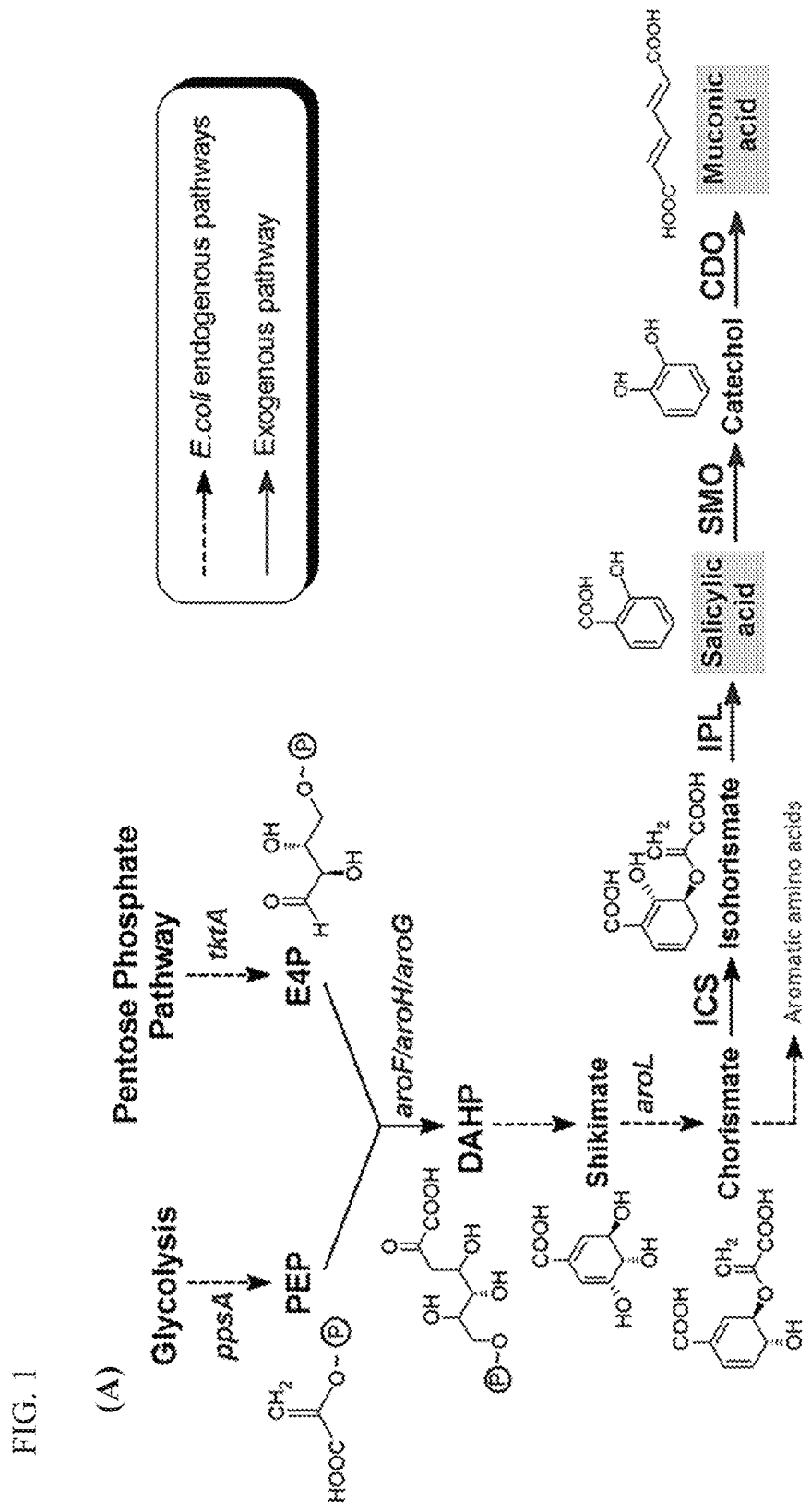
FIG. 1 shows a novel artificial pathway for the biosynthesis of MA. (A) Solid arrows indicate native metabolic pathways in *E. coli*; dashed arrows indicate the introduced artificial pathway. ICS, isochorismate synthase; IPL, isochorismate pyruvate lyase; SMO, salicylate 1-monooxygenase; CDO, catechol 1,2-dioxygenase. (B) Includes a delineation of an EP module (an exemplary "synthetic" enzymatic module), an NC module (an exemplary "degradative" enzymatic module), and an APTA module (an exemplary "precursor enhancing" enzymatic module) of a novel artificial pathway for the biosynthesis of MA.
Figure 1:
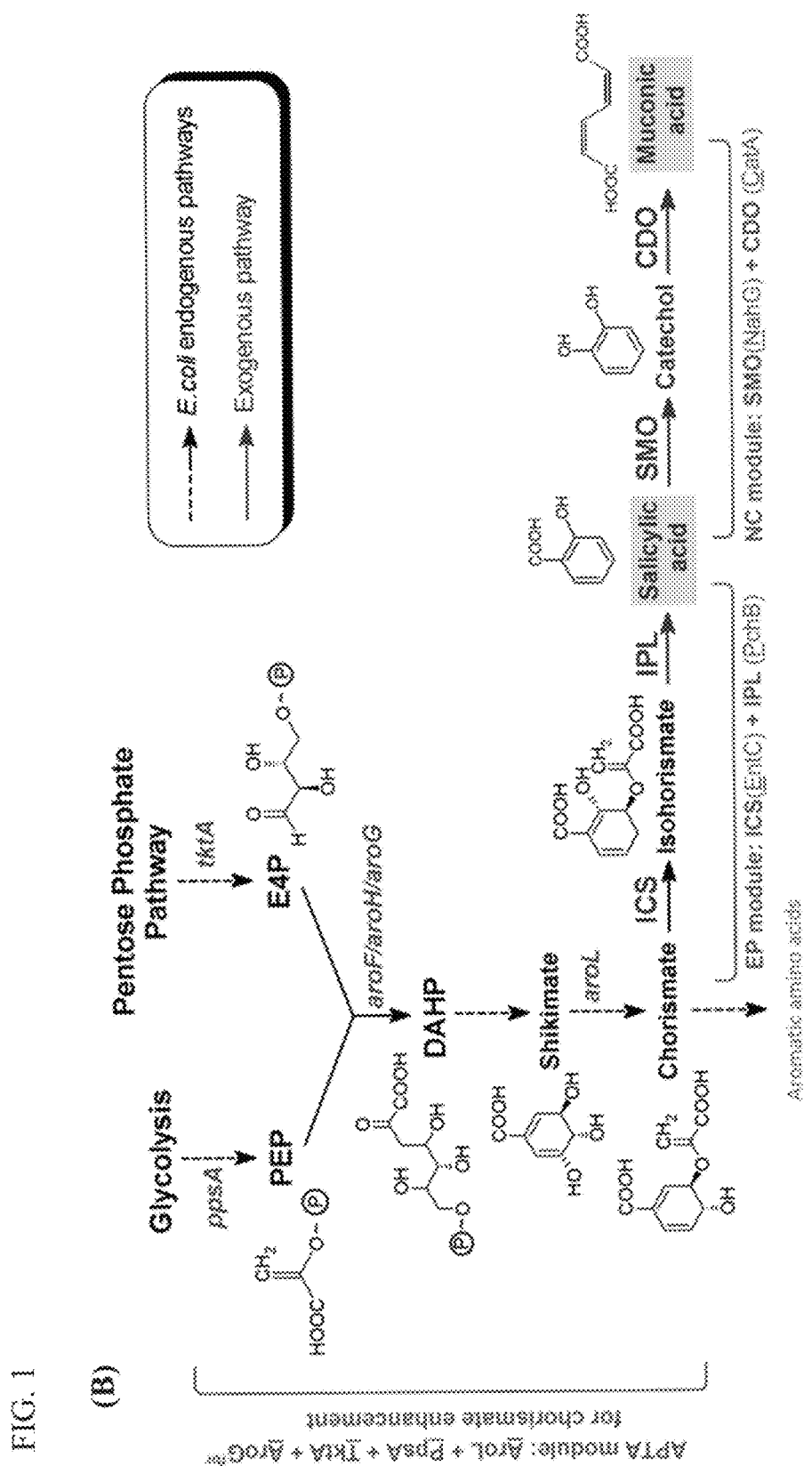

An illustrative biosynthetic pathway is shown in FIG. 1.

Biosynthetic Pathway

The biosynthetic pathway that is engineered into the host microorganism includes at least two, and preferably three, enzymatic modules. In one embodiment, the genetically engineered organism includes, or is engineered to include, a first "synthetic" module, which supplies enzymatic activity to produce salicylic acid from chorismate, and a second "degradative" module, which supplies enzymatic activity to produce muconic acid from salicylic acid. In another embodiment, the genetically engineered organism further includes, or is engineered to include, a third "precursor enhancing" enzymatic molecule which increases availability of chorismate.

"Synthetic" module. A first module is associated with salicylic acid (SA) biosynthesis. Chorismate, for example, an intermediate of the shikimate pathway, can serve as starting material for the enzymatic synthesis of salicylic acid. Chorismate can be used as a substrate by synthase, such as an isochorismate synthase (ICS) to produce isochorismate. The isochorismate produced can be converted to salicylic acid by the action of a lyase, such as an isochorismate pyruvate lyase (IPL). An exemplary synthetic module can thus include one or more polynucleotides that operably encode isochorismate synthase (ICS) activity and one or more polynucleotides that operably encode isochorismate pyruvate lyase (IPL) activity. A preferred synthetic module expresses an isochorismate synthase (ICS) and an isochorismate pyruvate lyase (IPL) to achieve SA biosynthesis, but other enzymes capable of catalyzing the conversion of chorismate to salicylic acid can be used.

The isochorismate synthase (ICS) that converts chorismate to isochorismate may be any enzyme having ICS activity. Enzymes having ICS activity are known to the skilled worker and are readily obtained. Examples include, but are not limited to, enzymes encoded by pchA from *P. aeruginosa*, entC from *E. coli*, and menF from *E. coli*. In one embodiment, the sequence of the ICS can be SEQ ID NO:1; however, the ICS of the invention is not limited to any particular ICS enzyme. Enzymes having ICS activity may also be obtained from *Mycobacterium* species and other *Pseudomonas* species, as well as other genera.

The isochorismate pyruvate lyase (IPL) that uses isochorismate as a substrate and converts it to salicylic acid may be any enzyme having IPL activity. Such enzymes are known to the skilled worker and are readily obtained. Examples include, but are not limited to, enzymes encoded by pchB from *P. aeruginosa* and/or *P. fluorescence*. In one embodiment, the sequence of the IPL can be SEQ ID NO:2; however, the IPL of the invention is not limited to any particular IPL enzyme. Enzymes having isochorismate pyruvate lyase activity may also be obtained from *Mycobacterium* species and other *Pseudomonas* species, as well as other genera.

Preferred enzymes are EntC from *E. coli* (SEQ ID NO:1) and the PchB from *P. fluorescence* (SEQ ID NO:2), which represent highly efficient ICS and IPL, respectively. Exemplary polynucleotides which encode the preferred enzymes are entC and pchB, respectively. In *E. coli*, the synthetic module preferably expresses entC and pchB and is for that reason termed the "EP module" in Example I. Exemplary components of the synthetic module are described in more detail in Example I and also, for example, in Lin et al., 2013 *Nat. Commun.* 4:2603; and US Patent Application Publication No. 2014/0370557, published Dec. 18, 2014; each of which is incorporated by reference herein.

"Degradative" module. A second module is associated with converting salicylic acid (SA) into muconic acid (MA). Salicylic acid can be used as a substrate for an oxygenase, such as a monoxygenase (MO) or a dioxygenase (DO), such as a salicylate 1-monoxygenase (SMO), to produce catechol. The catechol produced can be converted to muconic acid by the action of an oxygenase, such as a monoxygenase (MO) or a dioxygenase (DO), such as catechol 1,2-dioxygenase (CDO). An exemplary degradative module can thus include one or more polynucleotides that operably encode salicylate 1-monoxygenase (SMO) activity and one or more polynucleotides that operably encode catechol 1,2-dioxygenase (CDO) activity. A preferred degradative module expresses a salicylate 1-monoxygenase (SMO) and a catechol 1,2-dioxygenase (CDO) to convert SA to MA, but other enzymes capable of catalyzing the conversion of SA to MA can be used.

The salicylate 1-monoxygenase (SMO) that converts salicylic acid to catechol may be any enzyme having SMO activity. Enzymes having SMO activity are known to the skilled worker and are readily obtained. In one embodiment, the sequence of the SMO can be SEQ ID NO:3; however, the SMO of the invention is not limited to any particular SMO enzyme. Examples include, but are not limited to, enzymes encoded by nahG from *P. putida* DOT-T1E, paantABC from *P. aeruginosa* PAO1, pfantABC from *P. fluorescens* Migula, and ppbenABCD from *P. putida* KT2440. Enzymes having SMO activity may also be obtained from other *Pseudomonas* species, as well as other genera.

Two anthranilate 1,2-dioxygenases (ADOs) from *P. aeruginosa* PAO1 (encoded by paantABC) and *P. fluorescens* Migula (encoded by pfantABC) and a benzoate 1,2-dioxygenase (BDO) from *P. putida* KT2440 (encoded by ppbenABCD) can catalyze the conversion of anthranilate to catechol (Sun et al., 2013 *Appl. Environ. Microbiol.* 79:4024-30). Given the structure similarity of the substrates anthranilate (2-aminobenzoate) and SA (2-hydroxybenzoate), these enzymes are also considered as having SMO activity. Thus, enzymes having SMO activity can include dioxygenases such as anthranilate dioxygenase (ADO) and benzoate dioxygenase (BDO). Enzymes having SMO activity may also be obtained from other *Pseudomonas* species, as well as other genera.

The catechol 1,2-dioxygenase (CDO) that converts catechol to muconic acid may be any enzyme having CDO activity. Enzymes having CDO activity are known to the skilled worker and are readily obtained. In one embodiment, the sequence of the CDO can be SEQ ID NO:4; however, the CDO of the invention is not limited to any particular CDO enzyme. Examples include, but are not limited to, enzymes encoded by catA from *P. putida* KT-2440 and/or *P. aeruginosa*. Enzymes having CDO activity may also be obtained from other *Pseudomonas* species, as well as other genera.

Preferred enzymes are NahG from *E. coli* (SEQ ID NO:3) and the CatA from *P. putida* (SEQ ID NO:4), which represent highly efficient SMO and CDO, respectively. In one embodiment, the SMO can be encoded by SEQ ID NO:5; however, the invention is not limited to any particular sequence encoding the SMO enzyme. In one embodiment, the CDO can be encoded by SEQ ID NO:6; however, the invention is not limited to any particular sequence encoding the CDO enzyme. Exemplary polynucleotides which encode the preferred enzymes are nahG (preferably a codon-optimized version thereof; SEQ ID NO:5) and catA (SEQ ID NO:6), respectively. In *E. coli*, the degradative module preferably expresses nahG and catA, and is for that reason termed the "NC module" in Example I. Exemplary components of the degradative module are described in more detail in Example 1.

"Precursor Enhancing" Module. An optional third module is associated with enhanced chorismate availability. The optional "precursor enhancing" module operably encodes one or more enzymes that increase chorismate availability. Pathways such as the glycolysis pathway and the pentose phosphate pathway can be extended to feed into the shikimate pathway which can be used to enhance chorismate production (FIG. 1). Several rate limiting steps in the production of chorismate are known and can be manipulated to result in a microbe that produces more chorismate. Preferably, the precursor enhancing module expresses one or more enzymes that increase carbon flow toward chorismate. Enzymes that increase carbon flow toward chorismate are known to the skilled worker and are readily obtained. Exemplary enzymes include, but are not limited to, shikimate kinase, phosphoenolpyruvate synthase, transketolase, and 3-deoxy-D-arabino-heptulosonate-7-phosphate synthase, preferably feedback-inhibition-resistant 3-deoxy-D-arabino-heptulosonate-7-phosphate synthase, 3-dehydroquinate synthase, 3-dehydroquinate dehydratase, shikimate dehydrogenase, 3-phosphoshikimate-1-carboxyvinyltransferase, and chorismate synthase. Examples include, but are not limited to, AroL, AroF, AroH, AroG, PpsA, and TktA. In some embodiments, one or more of the AroL, AroF, AroH, AroG enzymes may be in the form of feedback-inhibition-resistant (fbr) enzymes. In one embodiment, the sequence of the AroL can be SEQ ID NO:7; however, the AroL of the invention is not limited to any particular AroL enzyme. In one embodiment, the sequence of the PpsA can be SEQ ID NO:8; however, the PpsA of the invention is not limited to any particular PpsA enzyme. In one embodiment, the sequence of the TktA can be SEQ ID NO:9; however, the TktA of the invention is not limited to any particular TktA enzyme. In one embodiment, the sequence of the AroG$^{fbr}$ can be SEQ ID NO:10; however, the AroG$^{fbr}$ of the invention is not limited to any particular AroG$^{fbr}$ enzyme. Preferred enzymes operably encoded by a precursor enhancing module are AroL (SEQ ID NO:7), PpsA (SEQ ID NO:8), TktA (SEQ ID NO:9), and a feedback-inhibition-resistant AroG (SEQ ID NO:10) from *E. coli*. Exemplary polynucleotides which encode preferred enzymes are aroL, ppsA, tktA, and aroG$^{fbr}$, respectively. In *E. coli*, the precursor enhancing module preferably expresses aroL, ppsA, tktA, and aroG$^{fbr}$ to increase chorismate availability, and for that reason is termed the "APTA module" in Example I. Exemplary components of the precursor enhancing module are described in more detail in Example I and also, for example, in Lin et al., 2013 *Nat. Commun.* 4:2603; and US Patent Application Publication No. 2014/0370557, published Dec. 18, 2014; each of which is incorporated by reference herein.

The enzymes expressed from the modules may be heterologous with respect to the host organism, or they may be naturally found in the host organism. For example, when *E. coli* is a host organism, one or more on the enzymes that are expressed from the one or more modules can be native *E. coli* enzymes, and one or more of the expressed enzymes can be from other (non-*E. coli*) organisms (i.e., heterologous). When an enzyme that is native to the host organism is expressed from a module, that enzyme is overexpressed in the host organism relative to a host organism without the module. Overexpression of naturally occurring enzymes, and expression of enzymes from other hosts, via the multiple modules, allows optimization and fine-tuning of the various enzymes that make up the overall genetically engineered biosynthetic pathway.

Host Cells

The novel metabolic pathway described herein is introduced into a host cell using genetic engineering techniques. The term "cell" is meant to include any type of biological cell. The host cell can be a eukaryotic cell or a prokaryotic cell. Preferably, the host cell is a prokaryotic cell such as a bacterial cell; however single cell eukaryotes such as protists or yeasts are also useful as host cells. Preferred host cells are microbial cells, preferably the cells of single-celled microbes such as bacterial cells or yeast cells, and are also referred to herein as "microorganisms." Exemplary host microorganisms that can be metabolically engineered to incorporate the biosynthetic pathway described herein include *Escherichia, Salmonella, Clostridium, Zymomonas, Pseudomonas, Bacillus, Rhodococcus, Alcaligenes, Klebsiella, Paenibacillus, Lactobacillus, Enterococcus, Arthrobacter, Brevibacterium, Corynebacterium Candida, Hansenula, Pichia* and *Saccharomyces*. Preferred hosts include *Escherichia coli, Bacillus subtilis Bacillus licheniformis, Alcaligenes eutrophus, Rhodococcus erythropolis, Paenibacillus macerans, Pseudomonas putida, Enterococcus faecium, Saccharomyces cerevisiae, Lactobacillus plantarum, Enterococcus gallinarium* and *Enterococcus faecalis*.

A cell that has been genetically engineered as described herein for muconic acid biosynthesis may be referred to as a "host" cell, a "recombinant" cell, a "metabolically engineered" cell, a "genetically engineered" cell or simply an "engineered" cell. These and similar terms are used interchangeably. As used herein, "genetically engineered" refers to a cell into which has been introduced at least one exogenous polynucleotide and has been altered "by the hand of man." For example, "genetically engineered" refers to a cell that contains one or more artificial sequences of nucleotides which have been created through standard molecular cloning techniques to bring together genetic material that is not natively found together. DNA sequences used in the construction of recombinant DNA molecules can originate from any species. Alternatively, DNA sequences that do not occur anywhere in nature may be created by the chemical synthesis of DNA, and incorporated into recombinant molecules. "Genetically engineered" also refers to a cell that has been genetically manipulated such that one or more endogenous nucleotides have been altered. For example, a cell is a genetically engineered cell by virtue of introduction of an alteration of endogenous nucleotides into a suitable cell. For instance, a regulatory region, such as a promoter, could be altered to result in increased or decreased expression of an operably linked endogenous coding region.

Genetically engineered cells are also referred to as "metabolically engineered" cells when the genetic engineering modifies or alters one or more particular metabolic pathways so as to cause a change in metabolism. The goal of metabolic engineering is to improve the rate and conversion of a substrate into a desired product. General laboratory methods for introducing and expressing or overexpressing native and nonnative proteins such as enzymes in many different cell types (including bacteria, plants, and animals) are routine and well known in the art; see, e.g., Sambrook et al, *Molecular Cloning: A Laboratory Manual*, Cold Spring Harbor Laboratory Press (1989), and *Methods for General and Molecular Bacteriology*, (eds. Gerhardt et al.) American Society for Microbiology, chapters 13-14 and 16-18 (1994).

While certain embodiments of the method are described herein using *E. coli* as the microbe, the method is not limited to *E. coli* and there are a number of other options for microbes suitable for use in the method. Other suitable microbial hosts for the production of MA and SA include, but are not limited to, prokaryotes such as members of the genera *Escherichia, Salmonella, Bacillus, Corynebacterium*, and cyanobacteria, and eukaryotes such as fungi, including *Saccharomyces cerevisiae*.

Introduction of the Biosynthetic Pathway into a Cell

In one embodiment, the genetically engineered organism includes, or is engineered to include, a first "synthetic" module, which supplies enzymatic activity to produce salicylic acid from chorismate, and a second "degradative" module, which supplies enzymatic activity to produce muconic acid from salicylic acid. In another embodiment, the genetically engineered organism further includes, or is engineered to include, a third "precursor enhancing" enzymatic molecule which increases availability of chorismate.

The introduction of the novel biosynthetic pathway of the invention into a cell involves expression or overexpression of one or more enzymes included in the biosynthetic pathway described herein. An enzyme is "overexpressed" in a recombinant cell when the enzyme is expressed at a level higher than the level at which it is expressed in a comparable wild-type cell. In cells that do not express a particular endogenous enzyme, or in cells in which the enzyme is not endogenous (i.e., the enzyme is not native to the cell), any level of expression of that enzyme in the cell is deemed an "overexpression" of that enzyme for purposes of the present invention.

As will be appreciated by a person of skill in the art, overexpression of an enzyme can be achieved through a number of molecular biology techniques. For example, overexpression can be achieved by introducing into the host cell one or more copies of a polynucleotide encoding a desired enzyme. A polynucleotide encoding a desired enzyme may be integrated in the genetically engineered microorganism's chromosome, or present in the genetically engineered microorganism as an extrachromosomal element, such as a plasmid or episome. Each coding region may be on a separate plasmid, all coding regions may be on one plasmid, or different coding regions may be grouped together on some combination thereof.

In one embodiment of the method of making the genetically engineered microorganism and resultant engineered microorganism, the polynucleotides that operably encode the selected enzymes, which are engineered into the host organism, are present on one or more plasmids. A separate plasmid can be used for each module, or two or more modules can be combined on the same plasmid. As a result, the genetically engineered host organism may include one, two or three plasmids to form the complete biosynthetic pathway for synthesis of muconic acid.

In one embodiment, the genetically engineered microorganism contains a biosynthetic pathway for the production of muconic acid that has been optimized to produce enhanced carbon flux into the pathway. Contrary to common wisdom, since high copy number plasmids typically yield better results in biosynthetic pathways, it was surprisingly found that expression of the degradative module on a low copy number plasmid resulted in dramatically improved MA production. A preferred genetically engineered microorganism contains a synthetic module on a high copy number plasmid and a degradative module on a relatively low copy number plasmid. An example of a high copy number plasmid is a plasmid having a copy number of over 20, or over 40. An example of a low copy number plasmid is a plasmid having a copy number under 20, or under 10. A precursor enhancer module, such as an APTA module, is optionally included on either high copy number plasmid, a medium copy number plasmid, or a low copy number plasmid.

In one embodiment, a genetically engineered microorganism of the invention contains three plasmids: a first plasmid expressing enzymes associated with the biosynthesis of salicylic acid, preferably an isochorismate synthase (ICS) and an isochorismate pyruvate lyase (IPL); a second plasmid expressing enzymes associated with the degradation of salicylic acid and its conversion to muconic acid, preferably a salicylate 1-monooxygenase (SMO) and a catechol 1,2-dioxygenase (CDO); and optionally third plasmid expressing enzymes associated with enhanced chorismate availability, preferably expressing one or more of aroL, ppsA, tktA, and aroG$^{fbr}$, encoding shikimate kinase, phosphoenolpyruvate synthase, transketolase and feedback-inhibition-resistant 3-deoxy-D-arabino-heptulosonate-7-phosphate synthase, respectively.

In another embodiment, a genetically engineered microorganism of the invention contains two plasmids: a first plasmid expressing enzymes associated with the biosynthesis of salicylic acid, preferably an isochorismate synthase (ICS) and an isochorismate pyruvate lyase (IPL), and also expressing one or more enzymes associated with enhanced chorismate availability, preferably at least one of aroL, ppsA, tktA, and aroG$^{fbr}$; and a second plasmid expressing enzymes associated with the degradation of salicylic acid and its conversion to muconic acid, preferably a salicylate 1-monooxygenase (SMO) and a catechol 1,2-dioxygenase (CDO).

The use of modules for different sections of the overall biosynthetic pathway provides significant advantages. Initially, the modules can be incorporated into separate plasmids. Expression levels for the various modules (each module operably encoding one or more enzymes associated with a portion of the overall metabolic pathway) can be conveniently controlled and tested by means of plasmid copy number. When it is found that low copy number is effective or even preferred, as described below for the salicylic acid "degradation" portion of the novel muconic acid pathway (the degradation module), copy number in the host can be reduced, thereby minimizing the metabolic burden to the host cell and conserving resources. When it is found that two (or more) modules are preferably expressed at the same level, they can be combined on a single plasmid. For example, as described below, both the synthetic module involved in biosynthesis of salicylic acid and the precursor enhancing module associated with increased availability of chorismate can optionally be included on the same plasmid, as higher expression of the enzymes encoded in those modules is beneficial. Overall, the use of multiple modules allows production of the desired end product, in this case for example, muconic acid, to be optimized by testing different expression levels.

In some embodiments, the host organism may produce, or may have been engineered to overproduce one or more aromatic amino acids, preferably phenylalanine and tyrosine. Such a host organism is then optionally further engineered to interrupt one or more metabolic pathways that utilize chorismate in the production of aromatic acids, for example by eliminating or knocking out one or more genes responsible for the first committing catalytic steps in the biosynthesis of phenylalanine, tyrosine, and tryptophan, such as pheA, tyrA, and trpD, respectively. Preferably, only pheA and tyrA of the competing pathways are eliminated or knocked out; trpD is not disrupted.

Production of Salicylic Acid, Muconic Acid, Derivatives, and Downstream Metabolites With respect to methods, the invention includes not only methods for making the genetically engineered microbe, but also methods for using the genetically engineered microbe, for example to produce a desired biochemical. In one method, the genetically engineered microbe is cultured under conditions to produce a downstream metabolite of chorismate, preferably an organic acid, such as salicylic acid and/or muconic acid. Culturing can be small scale or large scale; it can be aerobic or anaerobic. Preferably, the genetically engineered organism is cultured in a large scale fermentation system. The salicylic acid, muconic acid or other metabolite is separated from the microorganism and optionally isolated and purified. The salicylic acid, muconic acid, or other metabolite can be isolated from the host cell, or it can be isolated from the cell supernatant. The salicylic acid, muconic acid, or other metabolite can be secreted by the host cell and then isolated or purified, or it can be removed or separated from the host cell by solubilization, permeabilization, enzymatic action, mechanical crushing, or any other method to separate the biochemical from the host cell or cellular components.

Muconic acid, salicylic acid or other metabolite produced by and optionally isolated from the host cell can be further chemically or enzymatically derivatized. Muconic acid is a potential platform chemical for the manufacture of several widely-used consumer plastics, and is a synthetic precursor of a number of commercially relevant compounds, including adipic acid, terephthalic acid, caprolactam, hexamethylenediamine, and adiponitrile. Salicylic acid is mainly used for producing pharmaceuticals, skincare and haircare products. Muconic acid, salicylic acid, and their derivatives or downstream metabolites can be incorporated into many different types of materials such as polymeric compounds, including heteropolymers, copolymers and block copolymers, for example polyethylene terephthalate (PET) and polyester, as well as pharmaceutical, cosmetic, detergent, and industrial compositions. Presently, commercial production of muconic acid, salicylic acid, and their various derivatives such as adipic acid and terephthalic acid predominantly relies on organic chemical synthesis using petroleum-derived chemicals as starting materials. A "green" synthesis of salicylic acid, muconic acid and other compounds using the microbial biosynthetic pathway described herein represents a novel, environmentally sound advance in the art.

The present invention is illustrated by the following examples. It is to be understood that the particular examples, materials, amounts, and procedures are to be interpreted broadly in accordance with the scope and spirit of the invention as set forth herein.

EXAMPLES

Example 1

**Extending Shikimate Pathway for the Production of Muconic Acid and its Precursor Salicylic Acid in *Escherichia coli*** cis,cis-Muconic acid (MA) and salicylic acid (SA) are naturally-occurring organic acids having great commercial value. MA is a potential platform chemical for the manufacture of several widely-used consumer plastics; while SA is mainly used for producing pharmaceuticals (for example, aspirin and lamivudine) and skincare and haircare products. At present, MA and SA are commercially produced by organic chemical synthesis using petro-derived aromatic chemicals, such as benzene, as starting materials, which is not environmentally friendly. Here, we report a novel approach for efficient microbial production of MA via extending shikimate pathway by introducing the hybrid of an SA biosynthetic pathway with its partial degradation pathway. First, we engineered a well-developed phenylalanine producing *Escherichia coli* strain into an SA overproducer by introducing isochorismate synthase and isochorismate pyruvate lyase. The engineered stain is able to produce 1.2 g/L of SA from simple carbon sources, which is the highest titer reported so far. Further, the partial SA degradation pathway involving salicylate 1-monoxygenase and catechol 1,2-dioxygenase is established to achieve the conversion of SA to MA. Finally, a de novo MA biosynthetic pathway is assembled by integrating the established SA biosynthesis and degradation modules. Modular optimization enables the production of 1.5 g/L MA within 48 h in shake flasks. This study not only establishes an efficient microbial platform for the production of SA and MA, but also demonstrates a generalizable pathway design strategy for the de novo biosynthesis of valuable degradation metabolites.

Fossil fuels supply the world with not only energy but also important feedstocks for chemical industry. However, the shrinking availability of fossil reserves and the deteriorating environment compel people to explore renewable alternatives for the production of fuels, chemicals, and pharmaceuticals. Fortunately, the metabolic diversity of biological systems provides us with an extremely rich chemical repertoire. In recent years, the development of metabolic engineering has enabled the establishment of microbial chemical factories by constituting heterologous or non-natural biosynthetic pathways into genetically advantageous microbial hosts (Ajikumar et al., 2010 *Science* 330:70-4; Anthony et al., 2009 *Metab. Eng.* 11:13-9; Atsumi et al., 2008 *Metab. Eng.* 10:305-11; Huang et al., 2013 *Biotechnol. Bioeng.* 110:3188-96; Lin et al., 2013 *Metab. Eng.* 18:69-77; Lin et al., 2012 *Microb. Cell Fact.* 11:42; Shen et al., 2008 *Metab. Eng.* 10:312-20; Shen et al., 2012 *J. Ind. Microbiol. Biotechnol.* 39:1725-9; Zhang et al., 2008 *Proc. Natl. Acad. Sci. U.S.A.* 105:20653-8). In this study, we report our work on extending shikimate pathway for the production of two industrially important chemicals, cis,cis-muconic acid (MA) and its biosynthetic precursor salicylic acid (SA) in *Escherichia coli*.

MA is a platform chemical that serves as the precursor to several bio-plastics. It can be easily converted into adipic acid by chemical hydrogenation, and the latter one is a direct building block for nylon-6,6 and polyurethane (Sun et al., 2013 *Appl. Environ. Microbiol.* 79:4024-30). In addition, MA is a synthetic precursor to terephthalic acid, a chemical used for manufacturing polyethylene terephthalate (PET) and polyester (Curran et al., 2013 *Metab. Eng.* 15:55-66). The global production of adipic acid and terephthalic acid is 2.8 and 71 million metric tons, respectively (Curran et al., 2013 *Metab. Eng.* 15:55-66). SA is an important drug precursor mainly used for producing pharmaceuticals such as aspirin and lamivudine (an anti-HIV drug). SA esters and salts used in sunscreens and medicaments account for another large portion of SA consumption. The global market for SA products was estimated to be $292.5 million in 2012 and is expected to reach $521.2 million in 2019, growing at an annual increase of 8.6% ("Salicylic Acid Market for Pharmaceutical, Skin care, Hair care and Other Applications-Global Industry Analysis, Size, Share, Growth, Trends, and Forecast 2013-2019," 2013 Transparency Market Research). Currently, commercial production of adipic acid, terephthalic acid, and SA predominantly relies on organic chemical synthesis using petroleum-derived chemicals such as benzene as starting materials. These chemical synthesis processes are considered nonrenewable and environmentally unfriendly. Therefore, it is of great importance to develop "green" synthetic approaches that can utilize renewable feedstocks.

In fact, MA and SA are both naturally-occurring metabolites. MA is an intermediate in the microbial degradation of aromatic hydrocarbons (Fuchs et al., 2011 *Nat. Rev. Microbiol.* 9:803-16); while SA serves not only as a plant hormone (Chen et al., 2009 *Plant Signal Behav.* 4:493-6) but also as a biosynthetic precursor of bacterial siderophore (Gaille et al., 2002 *J. Biol. Chem.* 277:21768-75). In past 20 years, many efforts have been made for the microbial production of MA. Draths and Frost reported the earliest study on the artificial biosynthesis of MA in *Escherichia coli* from renewable carbon source glucose (Draths et al., 1994 *J. Am. Chem. Soc.* 116:399-400). By introducing three heterologous enzymes 3-dehydroshikimate dehydratase, protocatechuic acid decarboxylase and catechol 1,2-dioxygenase (CDO), the carbon flux was redirected from the *E. coli* native shikimate pathway to the biosynthesis of MA. Metabolically optimized strains carrying this artificial pathway were able to produce up to 2.4 g/L of MA via two-stage bioconversion in shake flasks (Draths et al., 1994 *J. Am. Chem. Soc.* 116:399-400) and 38.6 g/L via fed-batch fermentation (Niu et al., 2002 *Biotechnol. Prog.* 18:201-11). Afterwards, the same pathway was reconstituted in *Saccharomyces cerevisiae* (Weber et al., 2012 *Appl. Environ. Microbiol.* 78:8421-30), and the highest titer reported was nearly 141 mg/L (Curran et al., 2013 *Metab. Eng.* 15:55-66). Very recently, our group reported the construction of a different artificial pathway in *E. coli* by shunting tryptophan biosynthesis from anthranilate, which led to the production of 389 mg/L MA in shake flasks (Sun et al., 2013 *Appl. Environ. Microbiol.* 79:4024-30). By contrast, much less attention has been paid on engineering microbes for the production of SA, except for our recent work, in which SA was produced as a biosynthetic precursor to 4-hydroxycoumarin. Over-expression of heterologous enzymes isochorismate synthase (ICS) and isochorismate pyruvate lyase (IPL) in a wild-type *E. coli* strain resulted in the accumulation of 158.5 mg/L of SA in the culture (Lin et al., 2013 *Nat. Commun.* 4:2603).

In this example, we first reconstitute and optimize the biosynthesis of SA in *E. coli* by engineering a well-developed phenylalanine overproducing strain, yielding 1.2 g/L of SA, which is the highest titer reported so far. Further, the partial SA degradation pathway involving salicylate 1-monoxygenase (SMO) and catechol 1,2-dioxygenase (CDO) is established to achieve the conversion of SA to MA. On these bases, a novel MA biosynthetic approach is established by introducing the hybrid of the SA biosynthetic pathway and its partial degradation pathway (FIG. 1). Through modular optimization, the generated optimal strain produces about 1.5 g/L of MA in shake flasks. See also Lin et al. "Extending shikimate pathway for the production of muconic acid and its precursor salicylic acid in *Escherichia coli*," 2014 *Metab. Eng.* 23:62-69.

Materials and Methods

Media, Strains, and Plasmids

Luria-Bertani (LB) medium was used for inoculants preparation, cell propagation, and protein expression; while modified M9 medium was used for de novo microbial production of SA and MA. LB medium contains 10 g/L tryptone, 5 g/L yeast extract, and 10 g/L NaCl. The modified M9 (M9Y) medium contains 10 g/L glycerol, 2.5 g/L glucose, 6 g/L Na$_2$HPO4, 0.5 g/L NaCl, 3 g/L KH$_2$PO$_4$, 1 g/L NH$_4$Cl, 246.5 mg/L MgSO$_4$, 14.7 mg/L CaCl$_2$, 1 g/L yeast extract, 2 g/L MOPS, vitamin B1 (2.0 mg), H$_3$BO$_3$ (1.25 mg), NaMoO$_4$.2H$_2$O (0.15 mg), CoCl$_2$.6H$_2$O (0.7 mg), CuSO$_4$.5H$_2$O (0.25 mg), MnCl$_2$.4H$_2$O (1.6 mg), and ZnSO$_4$.7H$_2$O (0.3 mg). When needed, ampicillin, kanamycin, and chloramphenicol were added to the medium to the final concentrations of 100, 50, and 34 µg/ml, respectively. *E. coli* XL1-Blue was used as the host strain for plasmid construction and propagation. *E. coli* BW25113 was used as a wild-type (wt) strain for in vivo enzyme assays and feeding experiments. *E. coli* BL21 Star (DE3) was used for protein expression and purification. *E. coli* ATCC31884 is a phenylalanine overproducing strain purchased from American Type Culture Collection (ATCC) and was used for constructing the derivative strains SXX1 and QH4 (Huang et al., 2013 *Biotechnol. Bioeng.* 110:3188-96). pZE12-luc, pCS27, and pSA74 are high-, medium- and low-copy plasmids, respectively, used for expressing pathway enzymes. Plasmid pETDuet-1 was employed for protein expression and purification. The details of the strains and plasmids used in this study are depicted in Table 1.

TABLE 1

Strains and Plasmids used in this study.

| Strain | Genotype | Source |
|---|---|---|
| XL1-Blue | recA1 endA1 gyrA96 thi-1 hsdR17 supE44 relA1 lac [F' proAB lacIqZΔM15 Tn10 (Tet$^r$)] | Stratagene |
| BW25113 | rrnBT14 ΔlacZWJ16 hsdR514 ΔaraBADAH33 ΔrhaBADLD78 | CGSC |
| QH4 | *E. coli* ATCC31884 with pheA and tyrA disrupted | A |
| SXX1 | QH4 with trpD disrupted | This study |

| Plasmids | Description | Reference |
|---|---|---|
| pZE12-luc | PLlacO1, colE ori, luc, Amp$^r$ | B, D |
| pCS27 | PLlacO1, P15A ori, Kan$^r$ | B, D |
| pSA74 | PLlacO1, pSC101 ori, Cm$^r$ | B, D |
| pETDuet-1 | pT7, PBR322 ori, Amp$^r$ | Novagen |
| pZE-NahG | pZE12-luc containing nahG$^{opt}$ | This study |
| pZE-paantABC | pZE12-luc containing antABC from *P. aeruginosa* PAO1 | C |
| pZE-pfantABC | pZE12-luc containing antABC from *P. fluorescens* Migula | C |
| pZE-ppbenABCD | pZE12-luc containing benABCD from *P. putida* KT2440 | C |
| pET-NahG | pETDuet-1 containing nahG$^{opt}$ | This study |
| pZE-EP | pZE12-luc containing entC from *E. coli* and pchB from *P. fluorescens* Migula | B, D |
| pCS-EP | pCS27 containing entC from *E. coli* and pchB from *P. fluorescens* Migula | This study |
| pSA-EP | pSA74 containing entC from *E. coli* and pchB from *P. fluorescens* Migula | This study |
| pZE-NC | pZE12-luc containing nahG$^{opt}$ and catA from *P. putida* KT2440 | This study |
| pCS-NC | pCS27 containing nahG$^{opt}$ and catA from *P. putida* KT2440 | This study |
| pSA-NC | pSA74 containing nahG$^{opt}$ and catA from *P. putida* KT2440 | This study |
| pCS-APTA | pCS27 containing aroL, ppsA, tktA, aroG$^{fbr}$ from *E. coli* | B, D |
| pZE-EP-APTA | pZE12-luc containing PLlacO1-EP and PLlacO1-APTA | B, D |
| pZE-EP-NC | pZE12-luc PLlacO1-EP and PLlacO1-NC | This study |
| pCS-NC-APTA | pCS27 containing PLlacO1-NC and PLlacO1-APTA | This study |

A: Huang et al., 2013 *Biotechnol. Bioeng.* 110: 3188-96

B: Lin et al., 2013 *Nat. Commun.* 4: 2603

C: Sun et al., 2013 *Appl. Environ. Microbiol.* 79: 4024-30

D: US Patent Application Publication No. 2014/0370557, published Dec. 18, 2014

DNA Manipulation

Plasmids pZE-ppbenABCD, pZE-paantABC, pZE-pfantABC were constructed in our previous study (Sun et al., 2013 *Appl. Environ. Microbiol.* 79:4024-30). The codon-optimized gene nahG$^{opt}$ was synthesized and then subcloned into pZE12-luc vector using KpnI and XbaI, and into pETDuet-1 using NcoI and XhoI, yielding plasmids pZE-NahG and pET-NahG, respectively. The coding sequence of nahG$^{opt}$ (SEQ ID NO:5) is provided below:

```
Sequence of nahG^opt (SEQ ID NO: 5):
ATGCAGAACAGTACCAGCGCCCTGAACGTTAGCATCATTGGCGGCGGTAT
CGCAGGCGTTGCACTGGCCCTGGACTTATGTCGCCACGCCCACCTGAACG
TGCAGCTGTTCGAGGCAGCCCCGGCCTTTGGCGAAGTTGGTGCCGGTGTT
AGCTTCGGCGCCAATGCAGTGCGTGCAATCGCCGGTCTGGGTATCGCAGA
GCCGTACGGCAAAATTGCCGACAGTAATCCGGCCCCGTGGCAGGACATCT
GGTTCGAATGGCGCAATGGCCGTGATGCCAAATACCTGGGTTGCAGCGTT
GCCGAAGGCGTTGGTCAAAGCAGTGTGCACCGTGCCGATTTCCTGGACGC
TCTGGCTTCTCAGCTGCCGGACGGTATCGCTCAGTTCGGTAAACGTGCTC
AGCGTGTTGAACAGGACGGTGAGCAAGTGCGTGTGACATTCACAGACGGC
AGCGAGCACCGCTGCGATCTGCTGATTGGTGCCGACGGTATCAAGAGTAG
CATCCGTGACCACGTGTTACAGGGCCTGAATCAACCGCTGGCAAGCCCGC
GTTTTAGCGGCACCTGCGCCTATCGCGGTCTGATCGATAGCCAGCAGCTG
CGTGAGGCCTATCGTGCCCGTGGCGTGGACGAGCATCTGATTGACGTGCC
GCAGATGTACCTGGGCCTGGACGGCCACATCCTGACCTTCCCGGTTAAAC
AAGGCCGCCTGATCAACGTGGTGGCCTTCATCAGTGACCGCAGCCAACCG
AACCCGGTTTGGCCGAGCGATACACCGTGGGTTCGTAATGCCACCCAAGC
CGAGATGCTGGCCGCATTCGAGGGCTGGGATGATGCAGCCCAAGTGCTGC
TGGAGTGCATCCCGACCCCTAGTCTGTGGGCCCTGCACGACCTGGCAGAA
TTACCGGGCTACGTTCACGGCCGTGTTGGCTTAATCGGCGACGCCGCCCA
CGCAATGTTACCGCATCAGGGTGCCGGTGCAGGTCAGGGTCTGGAGGATG
CCTGGTTACTGGCCCGCCTGCTGGAAGACCCGAAGGTGCTGGACAAACGC
CCGCAGGCAGTGCTGGATGCCTATGACGCCGTTCGTCGTCCTCGTGCCTG
CCGTGTGCAGCGTACCAGCTTCGAGGCCGGCGAACTGTATGAGTTCCGTG
ACCCGGCCGTGTTAGCCGACGAGGAGCGTCTGGGCAAAGTTCTGGCCGAA
CGCTTTGACTGGCTGTGGAACCACGACATGCAGGAAGACTTATTACAGGC
CCGTGAGCTGCTGGGTTTACGTGCCCAAGCCGCCTAA
```

The plasmids pZE-EP, pCS-APTA, pZE-EP-APTA were constructed in our previous study (Lin et al., 2013 *Nat. Commun.* 4:2603). The expression cassette P$_L$lacO1-EP was amplified by PCR from pZE-EP and inserted into plasmids pCS27 and pSA74 between SacI and SpeI, yielding plasmids pCS-EP and pSA-EP, respectively. The gene catA was amplified from *Pseudomonas putida* KT2440 genomic DNA. Plasmid pZE-NC was created by subcloning nahG$^{opt}$ and catA into plasmid pZE12-luc using KpnI, XhoI, and XbaI. The expression cassette P$_L$lacO1-NC was amplified by PCR from pZE-NC and inserted into plasmid pCS27, pSA74, pZE-EP, and pCS-APTA between SacI and SpeI, yielding plasmids pCS-NC, pSA-NC, pZE-EP-NC (two operons) and pCS-NC-APTA (two operons).

Screening SMOs In Vivo

To evaluate the activity of enzymes converting SA to catechol, *E. coli* BW25113 was transformed with the expression vectors pZE-ppbenABCD, pZE-paantABC, pZE-pfantABC and pZE-NahG, separately. The resultant transformants were inoculated in 3 ml LB liquid medium containing 100 μg/ml of ampicillin and grown aerobically at 37° C. The overnight cultures were inoculated into 20 ml fresh LB medium and left to grow at 37° C. till OD$_{600}$ reached 0.6 and then induced with 0.25 mM of IPTG at 37° C. for additional 3 h. Then the cells were harvested, and re-suspended in M9Y medium (OD$_{600}$=2.1-2.7). SA was added into the cell suspension to a final concentration of 2 mM. The flasks were incubated with shaking at 37° C. for 10 min for the SMO encoded by nahG$^{opt}$ and 1 h for ppBenABCD, paAntABC, and pfAntABC. Samples were taken by removing cell pellets and the product (catechol) concentrations were measured with HPLC. The in vivo activity was expressed as μM/min/OD.

In Vitro SMO Enzyme Assay

To express and purify the enzyme, *E. coli* BL21 Star (DE3) was transformed with the expression plasmid pET-NahG. A fresh transformant was inoculated in 3 ml LB medium containing 100 μg/ml of ampicillin and grown aerobically at 37° C. Overnight cultures were inoculated into 50 ml fresh LB medium and left to grow at 37° C. till OD$_{600}$ reached 0.6 and then induced at 30° C. with 0.5 mM IPTG for another 3 h. Cells were then harvested and lysed by French Press. The recombinant protein with an N-terminal multi-histidine tag was purified using His-Spin protein miniprep kit (ZYMO RESEARCH). The enzyme concentration was measured using BCA kit (Pierce Chemicals). The standard enzyme assay was performed by making an assay mixture containing 500 μM NADH, 10 μM FAD, 0.97 nM purified enzyme, and SA as the substrate. The final volume was adjusted to 1 ml with Kpi buffer (20 mM, pH=7.0). The substrate concentrations varied from 0 to 100 μM. The reaction system was kept at 37° C. for 1 min and stopped by adding 50 μL HCl (20%). The reaction rates were calculated by measuring the formation of catechol via HPLC. The kinetic parameters were estimated with OriginPro8 through non-linear regression of the Michaelis-Menten equation.

Feeding Experiments

Feeding experiments were conducted to examine the production of MA from SA. *E. coli* BW25113 was transformed with the plasmid pZE-NC. Single colonies were inoculated into 3 ml LB medium containing 100 μg/ml ampicillin and grown aerobically at 37° C. 200 μl of overnight cultures were inoculated into 20 ml LB medium containing 100 μg/ml ampicillin. The cultures were left to grow at 37° C. till OD$_{600}$ reached 0.6 and then induced with 0.25 mM IPTG. After 3 h induction, cells were harvested, re-suspended in 20 ml of M9Y medium containing 3 mM of SA. Then SA was continuously fed into the cultures at 3 mM/h. Samples were taken at 2 h, 5 h and 10 h and the product concentrations were analyzed by HPLC.

De Novo Production of SA and MA

Overnight LB cultures of the producing strains were inoculated at 3% into the M9Y medium containing appropriated antibiotics and cultivated at 37° C. with shaking at 300 rpm. IPTG was added to the cultures to a final concentration of 0.25 mM at 0 h. Samples were taken every 24 hours. OD$_{600}$ values were measured and the concentrations of the products and intermediates were analyzed by HPLC.

HPLC Analysis

SA (from SIGMA ALDRICH), catechol (from Alfa Aesar), MA (from ACROS ORGANICS) were used as standards. Both the standards and samples were analyzed and quantified by HPLC (Dionex Ultimate 3000) equipped with a reverse phase ZORBAX SB-C18 column and an Ultimate 3000 Photodiode Array Detector. Solvent A was water with 0.1% formic acid, and solvent B was methanol. The column temperature was set to 28° C. The following gradient was used at a flow rate of 1 ml/min: 5 to 50% solvent B for 15 min, 50 to 5% solvent B for 1 min, and 5% solvent B for an additional 4 min. Quantification of SA, catechol, and MA was based on the peak areas at absorbance of specific wavelengths (329 nm for SA, 274 nm for catechol, and 260 nm for MA). Glucose, glycerol, and acetate were quantified using a previously described method (Shen et al., 2012 *J. Ind. Microbiol. Biotechnol.* 39:1725-9).

Results

A Novel Artificial Biosynthetic Pathway towards MA Production

SA is a widely occurring aromatic metabolite which is produced not only by plants as a phytohormone but also by some bacteria as an intermediate in the biosynthesis of siderophore (Chen et al., 2009 *Plant Signal Behav.* 4:493-6; Gaille et al., 2002 *J. Biol. Chem.* 277:21768-75). For its biosynthesis in bacteria, only two enzymes isochorismate synthase (ICS) and isochorismate pyruvate lyase (IPL) are required to synthesize SA from chorismate, a pivotal metabolite in shikimate pathway (Gaille et al., 2002 *J. Biol. Chem.* 277:21768-75; Gaille et al., 2003 *J. Biol. Chem.* 278:16893-8). In contrast, some bacterial species such as *Pseudomonas* were reported to be capable of utilizing SA as a carbon and energy source, during which SA is degraded via catechol and MA (Fuchs et al., 2011 *Nat. Rev. Microbiol.* 9:803-16; Seo et al., 2009 *Int. J. Environ. Res. Public. Health.* 6:278-309). In nature, however, the catabolism and anabolism of SA usually do not occur simultaneously in time and space. In this work, we reconstitute and synchronize the SA biosynthesis pathway catalyzed by ICS and IPL and its partial degradation pathway catalyzed by SMO and CDO, leading to a novel biosynthetic approach towards MA production from renewable carbon sources (FIG. 1).

Transformation of a Phenylalanine Overproducer to an SA Overproducer

Figure 2:
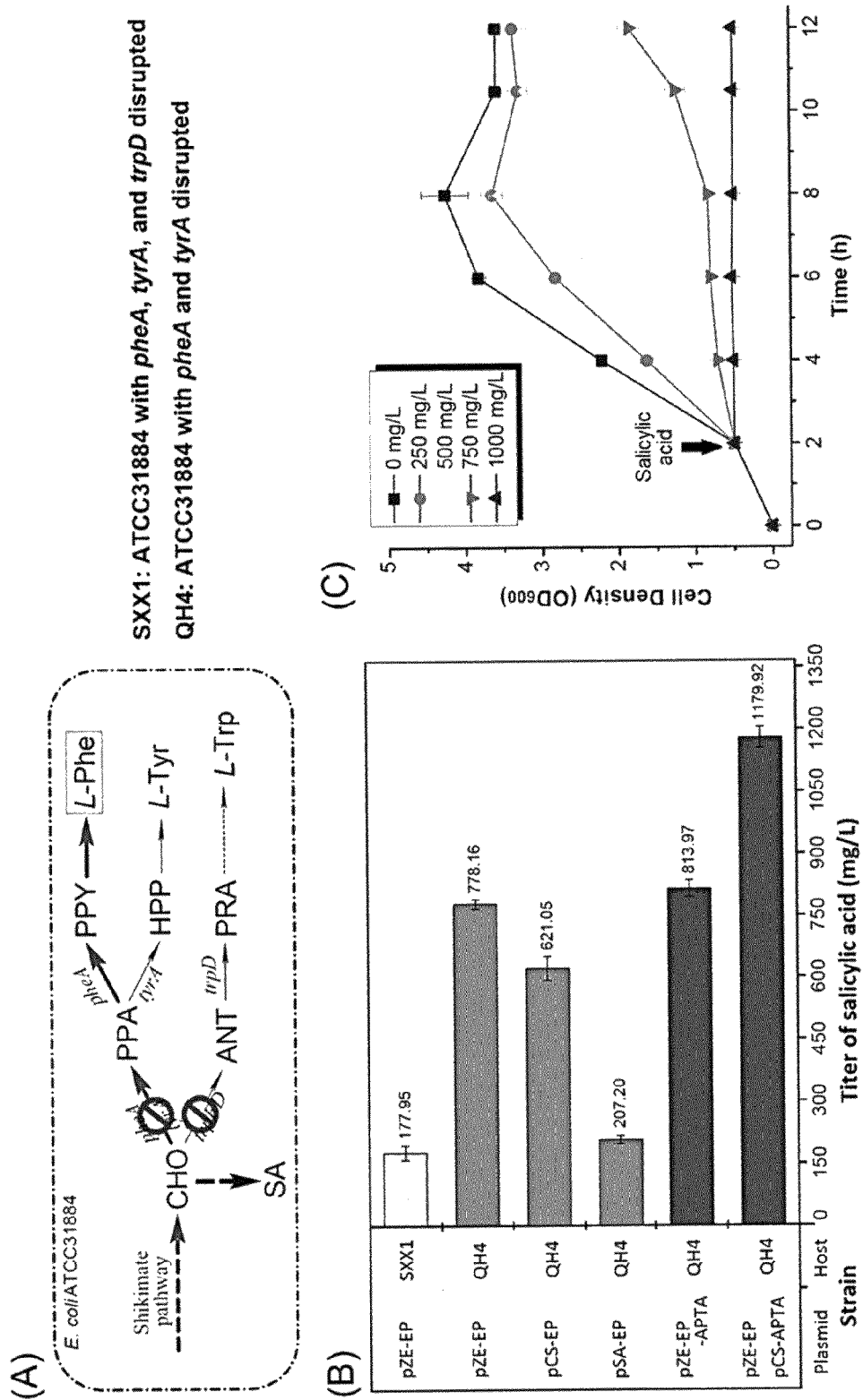
FIG. 2 shows transformation of a phenylalanine producing strain into an SA overproducer. (A) Schematic representation of the aromatic amino acid biosynthetic pathways in *E. coli*. Grey-colored arrows refer to the native carbon flow of *E. coli* strain ATCC31884, while the blue-colored arrow indicates the desired carbon flow after metabolic engineering. CHO, chorismate; PPA, prephenate; PPY, phenylpyruvate; HPP, 4-hydroxyphenylpyruvate; ANT, anthranilate; PRA, 5-phosphoribosyl-anthranilate. (B) Production of SA by metabolically engineered strains. pZE-EP, pCS-EP, and pSA-EP indicate that EntC and PchB are co-expressed using high-, medium-, and low-copy plasmids, respectively. All data points are reported as mean±s.d. from three independent experiments. (C) Growth inhibition assay to evaluate the toxicity of SA towards QH4 strain. All data points are reported as mean±s.d. from two independent experiments.

Re-directing carbon flux from the native shikimate pathway towards salicylate biosynthesis is the first step towards establishing the artificial MA biosynthetic pathway. Previously, we have reported that the EntC from *E. coli* and the PchB from *P. fluorescence* are the most efficient ICS and IPL, respectively, among all the screened enzymes. When EntC and PchB were co-expressed in wild type *E. coli* host, the resulting strain produced 158.5 mg/L of SA after 32-hour cultivation (Lin et al., 2013 *Nat. Commun.* 4:2603). To further elevate the production of SA, we focused on engineering a well-developed phenylalanine overproducing strain *E. coli* ATCC31884, since this strain has been successfully modified to produce tyrosine and caffeic acid efficiently (Huang et al., 2013 *Biotechnol. Bioeng.* 110: 3188-96; Patnaik et al., 2008 *Biotechnol. Bioeng.* 99:741-52). To eliminate undesired consumption of chorismate, we disrupted the competing pathway genes pheA, tyrA, and trpD from ATCC31884 which encode the enzymes responsible for the first committing catalytic steps in the biosynthesis of phenylalanine, tyrosine, and tryptophan, respectively, generating the strain SXX1 (FIG. 2A). However, when EntC and PchB were over-expressed in SXX1 with the high-copy plasmid (pZE-EP), the resulting strain only produced 177.95 mg/L of SA after 48 hour cultivation (FIG. 2B), which is not significantly improved compared with the wild type host strain carrying pZE-EP. Meanwhile, we observed that the final cell density of this mutant strain was quite low ($OD_{600}$=2.5), suggesting that the simultaneous disruption of pheA, tyrA and trpD impaired the cell growth.

Then we turned to another ATCC31884 derived strain QH4 with pheA and tyrA disrupted. QH4 carrying pZE-EP produced 778.16 mg/L SA by the end of 48 h. As we expected, the dramatic increase in SA production was accompanied by the improvement of cell growth (final $OD_{600}$=4.6). Further, to test the impact of plasmid copy number on SA production, we constructed another two plasmids pCS-EP (medium copy number) and pSA-EP (low copy number). As shown in FIG. 2B, QH4 carrying pCS-EP and pSA-EP produced 621.05 and 207.20 mg/L SA, respectively, indicating that the reduced copy number of plasmids used for expressing EntC and PchB resulted in lower production of SA. Therefore, high-level expression of the pathway enzymes is preferred to redirect more carbon flux into the artificial pathway. On this basis, we further boosted the availability of chorismate by eliminating the bottlenecks associated with the shikimate pathway. For this purpose, we employed a previously constructed chorismate-boosting plasmid expressing aroL, ppsA, tktA, and the feedback inhibition resistant mutant of aroG ($aroG^{fbr}$) (FIG. 1), namely pCS-APTA (medium copy number) (Lin et al., 2013 *Nat. Commun.* 4:2603). When pCS-APTA was co-transferred with pZE-EP into QH4, the resulting strain produced 1179.92 mg/L of SA at 48 h, a 51.6% increase in titer compared with its parent strain (QH4 containing pZE-EP). To our knowledge, this is the highest titer for SA production via microbial production approaches. However, when the APTA expression cassette was moved into the high-copy-number plasmid pZE-EP resulting in pZE-EP-APTA, the SA production of QH4 carrying pZE-EP-APTA (813.97 mg/L) was not improved significantly (FIG. 2B) compared with that of QH4 carrying pZE-EP alone. SA production for all the strains followed the growth-dependent pattern.

Figure 3:
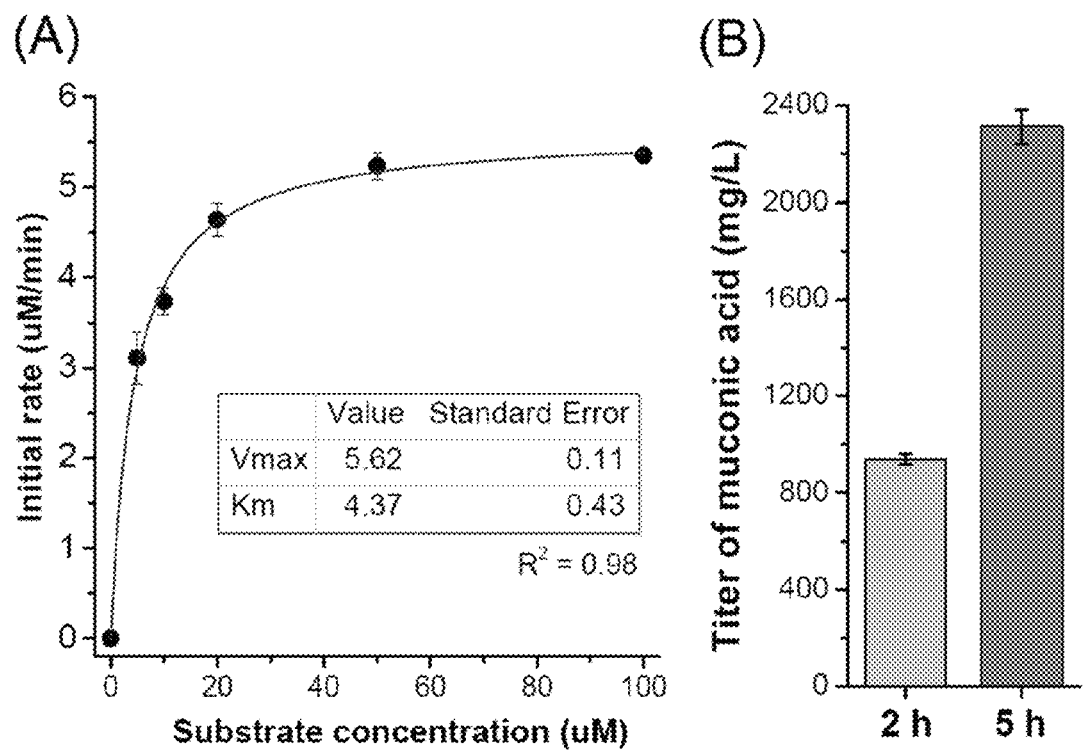
FIG. 3 shows activity of the salicylate 1-monoxygase (SMO) encoded by nahG$^{opt}$. (A) Kinetic parameters of the SMO. The $K_m$ and $V_{max}$ values were estimated with OriginPro8 through non-linear regression of the Michaelis-Menten equation. The protein concentration [E] of the SMO in the reaction systems was 0.97 nM. The $k_{cat}$ value was calculated according to the formula $k_{cat}=V_{max}/[E]$. All data points are reported as mean±s.d. from two independent experiments. (B) Conversion of SA to MA using the wild type *E. coli* strain carrying pZE-NC. Data points are reported as mean±s.d. from three independent experiments. Error bars are defined as s.d.

In addition, to evaluate the toxicity of SA against the host strain, a growth inhibition assay was conducted. We added SA into the cell cultures at different final concentrations ranging from 0-1000 mg/L and detected its impact on cell growth. As shown in FIG. 3C, SA exhibited toxicity against QH4 cells especially when its concentration exceeded 500 mg/L. 1000 mg/L SA completely inhibited the cell proliferation. Notably, strain QH4 carrying pZE-EP and pCS-APTA produced 1179.92 mg/L SA. This result suggested that on one hand QH4 can develop some degree of tolerance towards SA when the cells were initially exposed to low concentration of the produced SA; on the other hand, this strain has probably reached its maximum SA production capacity, which was constrained by its SA tolerance.

Screening for an Efficient SMO

Following the reconstitution and optimization of an SA biosynthetic pathway, our subsequent effort was focused on constructing the SA degradation pathway. SMO catalyzes the first enzymatic step of SA degradation, and thus it is of great importance to have an efficient SMO available for the pathway assembly. Pseudomonas species (for example, *P. putida*) are known to demonstrate diverse metabolism, especially their capability of degrading a variety of aromatic hydrocarbon pollutants (Seo et al., 2009 *Int. J. Environ. Res. Public. Health.* 6:278-309). A putative SMO (encoded by nahG) was identified from the genome of *P. putida* DOT-T1E. For the screening purpose, we synthesized a codon-optimized gene of $nahG^{opt}$. In addition, we have previously reported two anthranilate 1,2-dioxygenases (ADOs) from *P. aeruginosa* PAO1 (encoded by paantABC) and *P. fluorescens Migula* (encoded by pfantABC) and a benzoate 1,2- dioxygenase (BDO) from *P. putida* KT2440 (encoded by ppbenABCD) that can catalyzed the conversion of anthranilate to catechol (Sun et al., 2013 *Appl. Environ. Microbiol.* 79:4024-30). Given the structure similarity of the substrates anthranilate (2-aminobenzoate) and SA (2-hydroxybenzoate), these enzymes were also considered as candidates for SMO screening. To test their catalytic activities, the genes paantABC, pfantABC, ppBenABCD, and nahG$^{opt}$ were cloned into a high-copy-number plasmid pZE12-luc separately, resulting in the corresponding expression vectors used for in vivo assays. The wild type *E. coli* cells carrying these expression vectors were cultivated and then fed with 2 mM SA. Their activities were estimated by measuring the catechol formation rates. As indicated in Table 2, the SMO encoded by nahG$^{opt}$ showed the highest in vivo activity (54.78 µM/min/OD) among all the tested enzymes, while the ADOs and BDO also exhibited activity towards SA to generate catechol, although their catalytic activities were much lower.

Furthermore, to measure the kinetic parameters of the SMO encoded by nahG$^{opt}$, a multi-histidine tag was fused its N-terminus, and the recombinant protein was purified. The result of in vitro enzyme assay showed that the $K_m$ and $k_{cat}$ of the SMO were 4.37 µM and 96.56 s$^{-1}$, respectively, indicating its high substrate affinity and catalytic efficiency (FIG. 3A).

TABLE 2

In vivo activity of salicylate 1-monoxygenases from *Pseudomonas* species.

| Genes | Source | In vivo activity (µM/min/OD) |
|---|---|---|
| paantABC | P. aeruginosa | 0.17 ± 0.01 |
| pfantABC | P. fluorescence | 0.16 ± 0.01 |
| ppbenABCD | P. putida | 1.89 ± 0.02 |
| nahG$^{opt}$ | P. putida | 54.78 ± 1.65 |

Bioconversion of SA to MA

Conversion of SA to MA is a part of the SA degradation pathway, which involves the action of SMO and CDO. Given that an efficient CDO from *P. putida* KT-2440 (encoded by catA) has been identified previously in our lab (Sun et al., 2013 *Appl. Environ. Microbiol.* 79:4024-30), we aimed to assemble this pathway by co-expressing the SMO and the CDO in *E. coli*. For this purpose, the genes nahG$^{opt}$ and catA were cloned into a high-copy-number plasmid as an operon, yielding an expression vector pZE-NC. To explore its potential in the bioconversion of SA to MA, the wild type *E. coli* strain carrying pZE-NC was pre-cultivated in LB medium till the OD$_{600}$ values reached 4-4.5 and then transferred to M9Y medium containing 3 mM SA. Considering the toxicity issue, the concentration of SA was maintained below 500 mg/L (3.62 mM) by continuous feeding at 3 mM/h. By the end of 2 and 5 h, the titers of MA reached 938.4 and 2313.0 mg/L, respectively (FIG. 3B), indicating the high conversion rate from SA to MA with this plasmid construct.

Efficient De Novo MA Production via Modular Optimization

Figure 4:
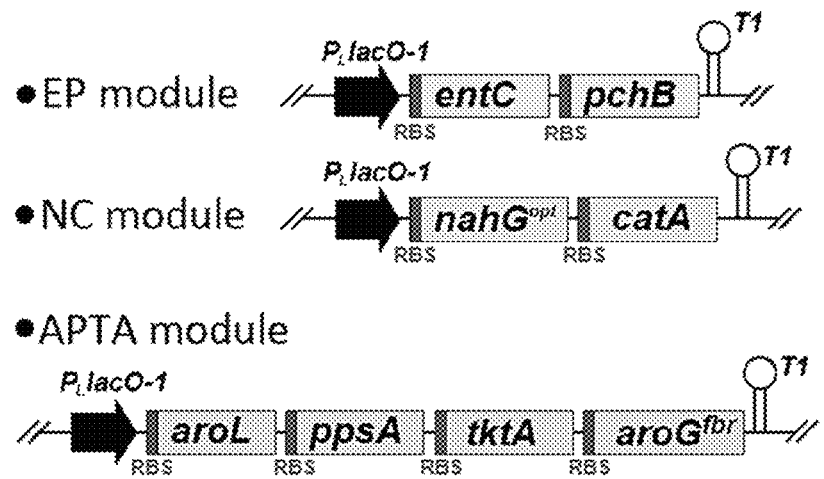
FIG. 4 shows modular optimization of the MA biosynthetic pathway. (A) Gene organization of the three modules: EP, NC, and APTA. entC, pchB, nahG$^{opt}$, and catA encode ICS, IPL, SMO, and CDO, respectively. (B) Optimization of MA production by adjusting the copy number of each module. All data points are reported as mean from three independent experiments. Asterisk mark indicates an untested construct.
Figure 4:
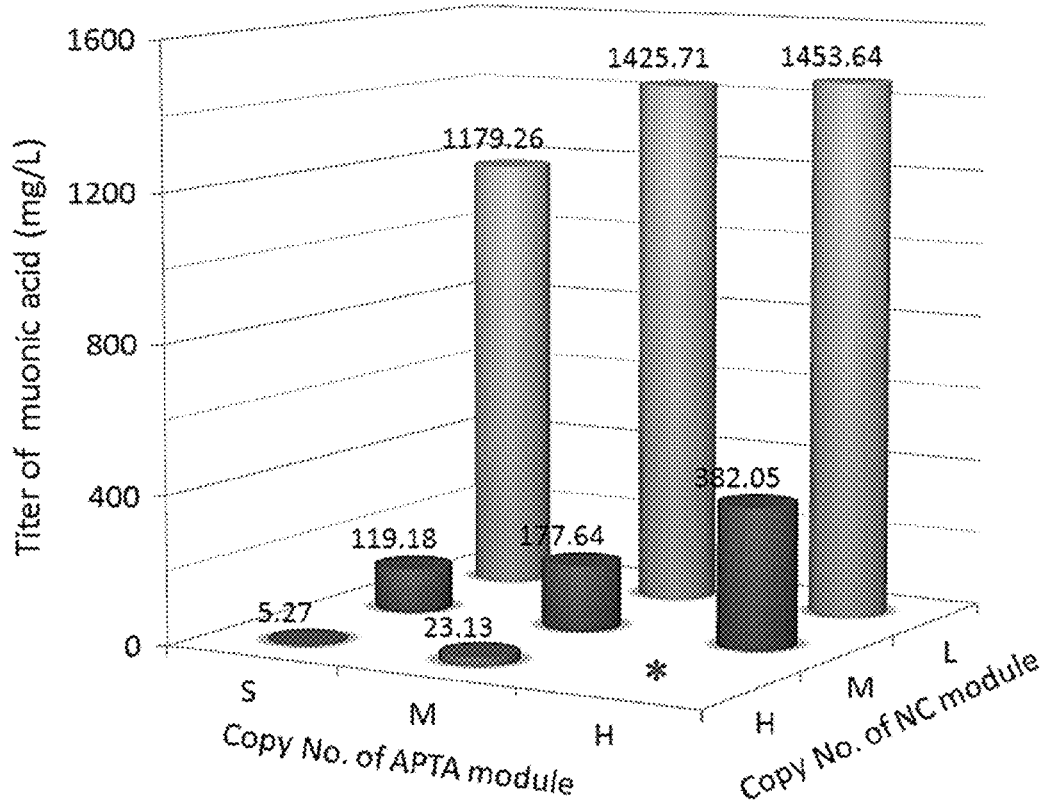

With the well-constructed SA biosynthesis and partial degradation pathways, we assembled the complete MA producing pathway by introducing the two modules simultaneously into *E. coli* using plasmid pZE-EP-NC, a high-copy expression vector with two operons. To our surprise, *E. coli* QH4 carrying pZE-EP-NC (Table 3, strain LS-1) only produced 5.27 mg/L MA after 48 h cultivation; while intermediates (SA and catechol) were not accumulated in the cultures. Besides, we observed that this strain underwent a longer lag phase before entering the exponential phase. We reasoned that the two modules were co-expressed in an unharmonious manner, which apparently exerted negative influence on the cell viability and productivity. To address this issue, we performed modular optimization to adjust the relative expression levels of each module. In this case, we decomposed the whole pathway into three modules (FIG. 4A), namely EP module (expressing entC and pchB responsible for SA biosynthesis), NC module (expressing nahG$^{opt}$ and catA responsible for converting SA to MA) and APTA module (expressing aroL, ppsA, tktA, and aroG$^{fbr}$ to increase chorismate availability). To ensure the maximum carbon flux towards the artificial pathway, the EP module was always fixed on high-copy plasmids. The expression level of NC module was optimized using high-, medium-, and low-copy plasmids. For APTA module, we attempted the high- and medium-copy expression in addition to the native expression (single copy). The plasmid combinations used for the modular optimization were listed in Table 3. As the result shown in Table 3 and FIG. 4B, compared with APTA module, NC module had much more impact on the performance of MA production. Expression of the NC module on a low-copy plasmid resulted in dramatically improved MA production, suggesting that relatively lower expression level of the NC module was more beneficial for this artificial pathway. Furthermore, over-expression of APTA module further enhanced the titer by about 20% (from LS6 to LS7 and LS8). Placing APTA module on the high-copy plasmid resulted in slightly higher MA production (1453.64 mg/L) than that on the medium-copy plasmid (1425.71 mg/L). Through modular optimization, the MA titer was improved by 275 folds compared with that of the initial test with strain LS-1. For all the MA producing strains, no accumulation of SA and catechol was observed, indicating the high robustness of NC module. We also analyzed the by-product accumulation and carbon source consumption for the best two strains LS-7 and LS-8. By the end of 48 h, Strain LS-8 consumed all the glucose (2.5 g/L) and glycerol (10 g/L), while strain LS-7 consumed all the glucose but left around 3 g/L glycerol unconsumed. Acetate was the major by-product for both strains (1.5-2.5 g/L). The OD$_{600}$ values and MA titers for the engineered *E. coli* strains at 24 h and 48 h are listed in Table 4.

TABLE 3

Combinations of plasmids for modular optimization.

| Strain name | Module Copy No. | | | Plasmid combinations | Titers (mg/L) |
|---|---|---|---|---|---|
| | EP | NC | APTA | | |
| LS-1 | H | H | S | pZE-EP-NC | 5.27 ± 1.14 |
| LS-2 | H | H | M | pZE-EP-NC, pCS-APTA | 23.13 ± 23.06 |
| LS-3 | H | M | S | pZE-EP, pCS-NC | 119.18 ± 23.15 |
| LS-4 | H | M | M | pZE-EP, pCS-NC-APTA | 177.64 ± 33.58 |
| LS-5 | H | M | H | pZE-EP-APTA, pCS-NC | 382.05 ± 30.62 |
| LS-6 | H | L | S | pZE-EP, pSA-NC | 1179.26 ± 61.58 |
| LS-7 | H | L | M | pZE-EP, pSA-NC, pCS-APTA | 1425.71 ± 41.08 |
| LS-8 | H | L | H | pZE-EP-APTA, pSA-NC | 1453.64 ± 98.88 |

*H, M and L indicate high-, medium-, and low-copy number plasmids; S refers to native expression with a single copy in the *E. coli* genome.

TABLE 4

The $OD_{600}$ values and MA titers for the engineered *E. coli* strains.

| Strain name | 24 h | | 48 h | |
|---|---|---|---|---|
| | $OD_{600}$ | Titer (mg/L) | $OD_{600}$ | Titer (mg/L) |
| LS-1 | 4.38 ± 1.50 | 3.35 ± 1.29 | 7.24 ± 0.50 | 5.27 ± 1.14 |
| LS-2 | 4.42 ± 2.51 | 29.52 ± 27.10 | 6.53 ± 0.49 | 23.13 ± 23.06 |
| LS-3 | 3.45 ± 0.19 | 83.38 ± 16.32 | 3.61 ± 0.28 | 119.18 ± 23.15 |
| LS-4 | 3.67 ± 0.32 | 60.20 ± 21.28 | 6.74 ± 0.07 | 177.64 ± 33.58 |
| LS-5 | 3.97 ± 0.46 | 100.09 ± 23.95 | 6.69 ± 0.54 | 382.05 ± 30.62 |
| LS-6 | 4.08 ± 0.19 | 418.84 ± 22.70 | 6.24 ± 0.26 | 1179.26 ± 61.58 |
| LS-7* | 3.16 ± 0.11 | 528.42 ± 9.03 | 4.82 ± 0.22 | 1425.71 ± 41.08 |
| LS-8* | 3.72 ± 0.84 | 638.40 ± 31.23 | 6.30 ± 0.23 | 1453.64 ± 98.88 |

*For LS-7 and LS-8, the OD600 values and MA titers at 72 h were slightly lower than those at 48 h.

Discussion

The extreme diversity of metabolism in living organisms generates an enormous number of natural products and metabolic intermediates, a substantial portion of which are of industrial and/or pharmaceutical importance. Over the past decades, metabolic engineering promoted the microbial production of a variety of valuable molecules, including bio-fuels, bulk chemicals, and pharmaceuticals (Oliver et al., 2013 *Proc. Natl. Acad. Sci. U.S.A.* 110:1249-54; Rabinovitch-Deere et al., 2013 *Chem. Rev.* 113:4611-32; Xu et al., 2013 *Curr. Opin. Biotechnol.* 24:291-299; Zhang et al., 2011 *ChemSusChem.* 4:1068-70). In this study, we devised a novel artificial pathway for the efficient production of MA by bridging the SA biosynthesis with its partial degradation pathway. In fact, biosynthesis and degradation of a specific molecule usually do not occur simultaneously in nature, since from the perspective of energy, it is not metabolically economic for organisms to survive nutrient-poor environment. But from the perspective of microbial production, it is a feasible strategy to link a degradation pathway to certain biosynthetic pathway and further to the microbial host's native metabolism, which can lead to the expansion of native metabolism and de novo production of a valuable degradation intermediate from inexpensive and renewable carbon sources. In addition to MA, we think this design strategy can also be generalized to establish the artificial biosynthesis of other degradation intermediates.

The shikimate pathway is the only route in bacteria leading to the biosynthesis of aromatic compounds. Before this study, two artificial pathways derived from the shikimate pathway have been reported for the microbial production of MA. Draths and Frost reported the first pathway that shunts the shikimate pathway via 3-dehydroshikimate by introducing three heterologous enzymes. To ensure high-level production, the competing pathway that consumes 3-dehydroshikimate was deleted. However, the knockout of shikimate dehydrogenase (aroE) disrupted not only the biosynthesis of aromatic amino acids but also the formation of other important aromatic molecules, such as 4-hydroxybenzoate, the precursor of the respiratory chain component, ubiquinol. Therefore, six supplements (L-phenylalanine, L-tyrosine, L-tryptophan, p-aminobenzoic acid, p-hydroxybenzoic acid, and 2,3-dihydroxybenzoic acid) were added in the fermentation medium to maintain the cell growth and high productivity, which increased the production cost (Draths et al., 1994 *J. Am. Chem. Soc.* 116:399-400; Niu et al., 2002 *Biotechnol. Prog.* 18:201-11). Recently, our group reported another MA producing pathway that shunts the tryptophan biosynthesis from anthranilate. This pathway keeps the integrity of the shikimate pathway, but involves a rate-limiting transamination step converting chorismate into anthranilate. This reaction requires the participation of glutamine, a less abundant amino acid, which limited the efficiency of the whole pathway (Sun et al., 2013 *Appl. Environ. Microbiol.* 79:4024-30). Comparatively, the pathway developed in this study does not disrupt the shikimate pathway either; meanwhile, all the catalytic steps in this pathway are very efficient. Although phenylalanine and tyrosine biosynthesis was deleted for high-level MA production, cell growth could be easily restored by supplementing a small amount of yeast extract (1 g/L).

In general, current metabolic engineering approaches towards the reconstitution of artificial pathways in heterologous hosts involve very limited regulatory mechanism, which frequently brings undesired effects. On one hand, unregulated expression of heterologous enzymes can cause cell toxicity and metabolic imbalance because of either the enzymes themselves or the toxic intermediates and products the enzymes generate. On the other hand, excessive expression of pathway enzymes can result in the waste of cellular resources and bring metabolic burden to the hosts, which may limit yield and productivity. Therefore, it is desirable to control the expression of pathway enzymes at a proper and balanced level. In recent years, the development of synthetic biology tools enabled the fine-tuning of protein expression level, including the adjustment of gene copy number (Lin et al., 2013 *Nat. Commun.* 4:2603), promoter strength (Hammer et al., 2006 *Trends Biotechnol.* 24:53-5), mRNA stability (Smolke et al., 2001 *Metab. Eng.* 3:313-21) and RBS binding efficiency (Salis et al., 2009 *Nat. Biotechnol.* 27:946-50). In addition, dynamic regulatory circuits were also developed to control pathway enzyme expression in response to the accumulation of certain intermediates (Dahl et al., 2013 *Nat. Biotechnol.* 31:1039-46; Zhang et al., 2012 *Nat. Biotechnol.* 30:354-9). These strategies were proved to be very effective for those relatively simple metabolic pathways. However, as artificial biosynthetic pathways become more complex, an increasing number of enzymes are involved in the pathway assembly. It becomes much more laborious and time-consuming to exhaustively explore the optimal expression level for each of the pathway enzymes simultaneously. In this study, we employed a simplified method of modular optimization to balance pathway enzyme expression. Using this approach, a multi-step pathway can be decomposed into several modules which can be initially optimized individually. Then the relative expression level of each module can be further adjusted in the context of the whole pathway. This strategy greatly reduces the number of engineering targets and combinations and has been used to achieve the efficient production of a variety of molecules (Ajikumar et al., 2010 *Science* 330:70-4; Juminaga et al., 2012 *Appl. Environ. Microbiol.* 78:89-98; Lin et al., 2013 *Nat. Commun.* 4:2603; Xu et al., 2013 *Nat. Commun.* 4:1409). In this work, the modular optimization enabled the improvement of MA production by 275 folds, which demonstrated its generalizable potential to the optimization of other complex pathways.

In conclusion, we established a novel MA biosynthetic pathway by connecting the SA biosynthesis with its partial degradation pathway and achieved the efficient production of MA and its precursor SA. However, cellular toxicity remains to be a challenge that limits the production of these chemicals, especially for SA. To address this issue, it is necessary to seek and develop more resistant *E. coli* strains. A recent work reported the engineering of efflux pumps which successfully improved the tolerance of *E. coli* toward non-native product n-butanol (Fisher et al., 2014 *ACS Synth. Biol.* 3:30-40). Besides, some microbial species other than *E. coli* exhibit high tolerance towards toxic chemicals, such as *Pseudomonas*. Given the increasing availability of genetic manipulation tools, it becomes more feasible to transfer and engineer the demonstrated pathways into these microorganisms.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

What is claimed is:

1. A genetically engineered microorganism comprising a genetically engineered metabolic pathway for the production of muconic acid from a salicylic acid intermediate, said pathway comprising:
   a first module expressing a plurality of enzymes associated with the biosynthesis of salicylic acid, said plurality of enzymes comprising an isochorismate synthase (ICS) and an isochorismate pyruvate lyase (IPL); and
   a second module expressing a plurality of enzymes associated with the conversion of salicylic acid to muconic acid, said plurality of enzymes comprising a salicylate 1-monoxygenase (SMO) and a catechol 1,2-dioxygenase (CDO).

2. The genetically engineered microorganism of claim 1 wherein the first and second modules are present on different plasmids.

3. The genetically engineered microorganism of claim 1 further comprising a third module expressing at least one enzyme that increases carbon flow toward chorismate.

4. The genetically engineered microorganism of claim 3 wherein the third module is present on a plasmid.

5. The genetically engineered microorganism of claim 4 wherein the first and third modules are present on a high copy number plasmid, and wherein the second module is present on a low copy number plasmid.

6. A method for producing organic acid, comprising:
   culturing the genetically engineered microorganism of claim 1 under conditions to produce a downstream metabolite of chorismate comprising an organic acid.

7. The method of claim 6 wherein the organic acid comprises salicylic acid.

8. The method of claim 6 wherein the organic acid comprises muconic acid.

9. The method of claim 6 further comprising separating the organic acid from the genetically engineered microorganism.

10. The method of claim 6 further comprising isolating and purifying the organic acid.

* * * * *

SEQUENCE LISTING

```
<160> NUMBER OF SEQ ID NOS: 10

<210> SEQ ID NO 1
<211> LENGTH: 391
<212> TYPE: PRT
<213> ORGANISM: Escherichia coli

<400> SEQUENCE: 1

Met Asp Thr Ser Leu Ala Glu Glu Val Gln Gln Thr Met Ala Thr Leu
1               5                   10                  15

Ala Pro Asn Arg Phe Phe Phe Met Ser Pro Tyr Arg Ser Phe Thr Thr
            20                  25                  30

Ser Gly Cys Phe Ala Arg Phe Asp Glu Pro Ala Val Asn Gly Asp Ser
        35                  40                  45

Pro Asp Ser Pro Phe Gln Gln Lys Leu Ala Ala Leu Phe Ala Asp Ala
    50                  55                  60

Lys Ala Gln Gly Ile Lys Asn Pro Val Met Val Gly Ala Ile Pro Phe
65                  70                  75                  80

Asp Pro Arg Gln Pro Ser Ser Leu Tyr Ile Pro Glu Ser Trp Gln Ser
                85                  90                  95

Phe Ser Arg Gln Glu Lys Gln Ala Ser Ala Arg Arg Phe Thr Arg Ser
            100                 105                 110

Gln Ser Leu Asn Val Val Glu Arg Gln Ala Ile Pro Glu Gln Thr Thr
        115                 120                 125

Phe Glu Gln Met Val Ala Arg Ala Ala Ala Leu Thr Ala Thr Pro Gln
    130                 135                 140

Val Asp Lys Val Val Leu Ser Arg Leu Ile Asp Ile Thr Thr Asp Ala
145                 150                 155                 160

Ala Ile Asp Ser Gly Val Leu Leu Glu Arg Leu Ile Ala Gln Asn Pro
                165                 170                 175

Val Ser Tyr Asn Phe His Val Pro Leu Ala Asp Gly Gly Val Leu Leu
            180                 185                 190

Gly Ala Ser Pro Glu Leu Leu Leu Arg Lys Asp Gly Glu Arg Phe Ser
        195                 200                 205

Ser Ile Pro Leu Ala Gly Ser Ala Arg Arg Gln Pro Asp Glu Val Leu
```

```
                        210                 215                 220
Asp Arg Glu Ala Gly Asn Arg Leu Leu Ala Ser Glu Lys Asp Arg His
225                 230                 235                 240

Glu His Glu Leu Val Thr Gln Ala Met Lys Glu Val Leu Arg Glu Arg
                245                 250                 255

Ser Ser Glu Leu His Val Pro Ser Pro Gln Leu Ile Thr Thr Pro
            260                 265                 270

Thr Leu Trp His Leu Ala Thr Pro Phe Glu Gly Lys Ala Asn Ser Gln
        275                 280                 285

Glu Asn Ala Leu Thr Leu Ala Cys Leu Leu His Pro Thr Pro Ala Leu
290                 295                 300

Ser Gly Phe Pro His Gln Ala Ala Thr Gln Val Ile Ala Glu Leu Glu
305                 310                 315                 320

Pro Phe Asp Arg Glu Leu Phe Gly Gly Ile Val Gly Trp Cys Asp Ser
                325                 330                 335

Glu Gly Asn Gly Glu Trp Val Val Thr Ile Arg Cys Ala Lys Leu Arg
            340                 345                 350

Glu Asn Gln Val Arg Leu Phe Ala Gly Ala Gly Ile Val Pro Ala Ser
        355                 360                 365

Ser Pro Leu Gly Glu Trp Arg Glu Thr Gly Val Lys Leu Ser Thr Met
370                 375                 380

Leu Asn Val Phe Gly Leu His
385                 390

<210> SEQ ID NO 2
<211> LENGTH: 122
<212> TYPE: PRT
<213> ORGANISM: Pseudomonas fluorescence

<400> SEQUENCE: 2

Met Leu Ala Phe Asp Pro Met Asn Phe Pro Leu Val Asp Pro Asp Met
1               5                   10                  15

Lys Thr Pro Glu Gln Cys Ser Gly Leu Asp Asp Val Arg Cys Gly Ile
            20                  25                  30

Asp Ala Met Asp Gln Gln Ile Ile Gln Ala Leu Gly Arg Arg Leu Ala
        35                  40                  45

Tyr Val Lys Ala Ala Ala Gln Phe Lys Pro Thr Glu Asp Ser Ile Ala
    50                  55                  60

Ala Pro Glu Arg Val Ala Ala Met Leu Pro Gln Arg Arg Gln Trp Ala
65                  70                  75                  80

Glu Gln Ala Ser Leu Asp Pro Met Phe Val Val Pro Leu Phe Ala Gln
                85                  90                  95

Ile Ile His Trp Asn Ile Ala Gln Gln Val Arg His Trp Arg Arg Gln
            100                 105                 110

His Gly Leu Asp Gln Gly Ala Gln Asp Glu
        115                 120

<210> SEQ ID NO 3
<211> LENGTH: 428
<212> TYPE: PRT
<213> ORGANISM: Escherichia coli

<400> SEQUENCE: 3

Met Gln Asn Ser Thr Ser Ala Leu Asn Val Ser Ile Ile Gly Gly Gly
1               5                   10                  15

Ile Ala Gly Val Ala Leu Ala Leu Asp Leu Cys Arg His Ala His Leu
```

```
            20                  25                  30
Asn Val Gln Leu Phe Glu Ala Ala Pro Ala Phe Gly Glu Val Gly Ala
        35                  40                  45
Gly Val Ser Phe Gly Ala Asn Ala Val Arg Ala Ile Ala Gly Leu Gly
    50                  55                  60
Ile Ala Glu Pro Tyr Gly Lys Ile Ala Asp Ser Asn Pro Ala Pro Trp
65                  70                  75                  80
Gln Asp Ile Trp Phe Glu Trp Arg Asn Gly Arg Asp Ala Lys Tyr Leu
                85                  90                  95
Gly Cys Ser Val Ala Glu Gly Val Gln Ser Ser Val His Arg Ala
            100                 105                 110
Asp Phe Leu Asp Ala Leu Ala Ser Gln Leu Pro Asp Gly Ile Ala Gln
        115                 120                 125
Phe Gly Lys Arg Ala Gln Arg Val Glu Gln Asp Gly Glu Gln Val Arg
    130                 135                 140
Val Thr Phe Thr Asp Gly Ser Glu His Arg Cys Asp Leu Leu Ile Gly
145                 150                 155                 160
Ala Asp Gly Ile Lys Ser Ser Ile Arg Asp His Val Leu Gln Gly Leu
                165                 170                 175
Asn Gln Pro Leu Ala Ser Pro Arg Phe Ser Gly Thr Cys Ala Tyr Arg
            180                 185                 190
Gly Leu Ile Asp Ser Gln Gln Leu Arg Glu Ala Tyr Arg Ala Arg Gly
        195                 200                 205
Val Asp Glu His Leu Ile Asp Val Pro Gln Met Tyr Leu Gly Leu Asp
    210                 215                 220
Gly His Ile Leu Thr Phe Pro Val Lys Gln Gly Arg Leu Ile Asn Val
225                 230                 235                 240
Val Ala Phe Ile Ser Asp Arg Ser Gln Pro Asn Pro Val Trp Pro Ser
                245                 250                 255
Asp Thr Pro Trp Val Arg Asn Ala Thr Gln Ala Glu Met Leu Ala Ala
            260                 265                 270
Phe Glu Gly Trp Asp Asp Ala Ala Gln Val Leu Leu Glu Cys Ile Pro
        275                 280                 285
Thr Pro Ser Leu Trp Ala Leu His Asp Leu Ala Glu Leu Pro Gly Tyr
    290                 295                 300
Val His Gly Arg Val Gly Leu Ile Gly Asp Ala Ala His Ala Met Leu
305                 310                 315                 320
Pro His Gln Gly Ala Gly Ala Gly Gln Gly Leu Glu Asp Ala Trp Leu
                325                 330                 335
Leu Ala Arg Leu Leu Glu Asp Pro Lys Val Leu Asp Lys Arg Pro Gln
            340                 345                 350
Ala Val Leu Asp Ala Tyr Asp Ala Val Arg Arg Pro Arg Ala Cys Arg
        355                 360                 365
Val Gln Arg Thr Ser Phe Glu Ala Gly Glu Leu Tyr Glu Phe Arg Asp
    370                 375                 380
Pro Ala Val Leu Ala Asp Glu Glu Arg Leu Gly Lys Val Leu Ala Glu
385                 390                 395                 400
Arg Phe Asp Trp Leu Trp Asn His Asp Met Gln Glu Asp Leu Leu Gln
                405                 410                 415
Ala Arg Glu Leu Leu Gly Leu Arg Ala Gln Ala Ala
            420                 425

<210> SEQ ID NO 4
```

<211> LENGTH: 311
<212> TYPE: PRT
<213> ORGANISM: Pseudomonas putida

<400> SEQUENCE: 4

```
Met Thr Val Lys Ile Ser His Thr Ala Asp Ile Gln Ala Phe Phe Asn
1               5                   10                  15

Arg Val Ala Gly Leu Asp His Ala Glu Gly Asn Pro Arg Phe Lys Gln
            20                  25                  30

Ile Ile Leu Arg Val Leu Gln Asp Thr Ala Arg Leu Ile Glu Asp Leu
        35                  40                  45

Glu Ile Thr Glu Asp Glu Phe Trp His Ala Val Asp Tyr Leu Asn Arg
50                  55                  60

Leu Gly Gly Arg Asn Glu Ala Gly Leu Leu Ala Ala Gly Leu Gly Ile
65                  70                  75                  80

Glu His Phe Leu Asp Leu Leu Gln Asp Ala Lys Asp Ala Glu Ala Gly
                85                  90                  95

Leu Gly Gly Gly Thr Pro Arg Thr Ile Glu Gly Pro Leu Tyr Val Ala
            100                 105                 110

Gly Ala Pro Leu Ala Gln Gly Glu Ala Arg Met Asp Asp Gly Thr Asp
        115                 120                 125

Pro Gly Val Val Met Phe Leu Gln Gly Gln Val Phe Asp Ala Asp Gly
130                 135                 140

Lys Pro Leu Ala Gly Ala Thr Val Asp Leu Trp His Ala Asn Thr Gln
145                 150                 155                 160

Gly Thr Tyr Ser Tyr Phe Asp Ser Thr Gln Ser Glu Phe Asn Leu Arg
                165                 170                 175

Arg Arg Ile Ile Thr Asp Ala Glu Gly Arg Tyr Arg Ala Arg Ser Ile
            180                 185                 190

Val Pro Ser Gly Tyr Gly Cys Asp Pro Gln Gly Pro Thr Gln Glu Cys
        195                 200                 205

Leu Asp Leu Leu Gly Arg His Gly Gln Arg Pro Ala His Val His Phe
210                 215                 220

Phe Ile Ser Ala Pro Gly His Arg His Leu Thr Thr Gln Ile Asn Phe
225                 230                 235                 240

Ala Gly Asp Lys Tyr Leu Trp Asp Asp Phe Ala Tyr Ala Thr Arg Asp
                245                 250                 255

Gly Leu Ile Gly Glu Leu Arg Phe Val Glu Asp Ala Ala Ala Ala Arg
            260                 265                 270

Asp Arg Gly Val Gln Gly Glu Arg Phe Ala Glu Leu Ser Phe Asp Phe
        275                 280                 285

Arg Leu Gln Gly Ala Lys Ser Pro Asp Ala Glu Ala Arg Ser His Arg
290                 295                 300

Pro Arg Ala Leu Gln Glu Gly
305                 310
```

<210> SEQ ID NO 5
<211> LENGTH: 1287
<212> TYPE: DNA
<213> ORGANISM: Artificial
<220> FEATURE:
<223> OTHER INFORMATION: codon-optimized nahG from E. coli

<400> SEQUENCE: 5

```
atgcagaaca gtaccagcgc cctgaacgtt agcatcattg gcggcggtat cgcaggcgtt    60
gcactggccc tggacttatg tcgccacgcc cacctgaacg tgcagctgtt cgaggcagcc   120
```

```
ccggcctttg gcgaagttgg tgccggtgtt agcttcggcg ccaatgcagt gcgtgcaatc        180
gccggtctgg gtatcgcaga gccgtacggc aaaattgccg acagtaatcc ggccccgtgg        240
caggacatct ggttcgaatg gcgcaatggc cgtgatgcca atacctgggt tgcagcgtt         300 gccgaaggcg ttggtcaaag cagtgtgcac cgtgccgatt tcctggacgc tctggcttct       360
cagctgccgg acggtatcgc tcagttcggt aaacgtgctc agcgtgttga acaggacggt       420
gagcaagtgc gtgtgacatt cacagacggc agcgagcacc gctgcgatct gctgattggt       480
gccgacggta tcaagagtag catccgtgac cacgtgttac agggcctgaa tcaaccgctg       540
gcaagcccgc gttttagcgg cacctgcgcc tatcgcggtc tgatcgatag ccagcagctg       600
cgtgaggcct atcgtgcccg tggcgtggac gagcatctga ttgacgtgcc gcagatgtac       660
ctgggcctgg acgccacat cctgaccttc ccggttaaac aaggccgcct gatcaacgtg       720
gtggccttca tcagtgaccg cagccaaccg aacccggttt ggccgagcga tacaccgtgg       780
gttcgtaatg ccacccaagc cgagatgctg gccgcattcg agggctggga tgatgcagcc       840
caagtgctgc tggagtgcat cccgaccct agtctgtggg ccctgcacga cctggcagaa       900
ttaccgggct acgttcacgg ccgtgttggc ttaatcggcg acgccgccca cgcaatgtta       960
ccgcatcagg gtgccggtgc aggtcagggt ctggaggatg cctggttact ggcccgcctg       1020
ctggaagacc cgaaggtgct ggacaaacgc ccgcaggcag tgctggatgc ctatgacgcc       1080
gttcgtcgtc ctcgtgcctg ccgtgtgcag cgtaccagct tcgaggccgg cgaactgtat       1140
gagttccgtg acccggccgt gttagccgac gaggagcgtc tgggcaaagt tctggccgaa       1200
cgctttgact ggctgtggaa ccacgacatg caggaagact tattacaggc ccgtgagctg       1260
ctgggtttac gtgcccaagc cgcctaa                                           1287
```

<210> SEQ ID NO 6
<211> LENGTH: 936
<212> TYPE: DNA
<213> ORGANISM: Pseudomonas putida

<400> SEQUENCE: 6

```
atgaccgtga aaatttccca cactgccgac attcaagcct tcttcaaccg ggtagctggc        60
ctggaccatg ccgaaggaaa cccgcgcttc aagcagatca ttctgcgcgt gctgcaagac       120
accgcccgcc tgatcgaaga cctggagatt accgaggacg agttctggca cgccgtcgac       180
tacctcaacc gcctgggcgg ccgtaacgag gcaggcctgc tggctgctgg cctgggtatc       240
gagcacttcc tcgacctgct gcaggatgcc aaggatgccg aagccggcct ggcggcggc       300 accccgcgca ccatcgaagg cccgttgtac gttgccgggg cgccgctggc ccagggcgaa       360
gcgcgcatga cgacggcac tgacccaggc gtggtgatgt ccttcagggg ccaggtgttc       420
gatgccgacg gcaagccgtt ggccggtgcc accgtcgacc tgtggcacgc caatacccag       480
ggcacctatt cgtacttcga ttcgacccag tccgagttca acctgcgtcg gcgtatcatc       540
accgatgccg agggccgcta ccgcgcgcgc tcgatcgtgc cgtccgggta ggctgcgac       600 ccgcagggcc caacccagga atgcctggac ctgctcggcc gccacggcca gcgcccggcg       660
cacgtgcact tcttcatctc ggcaccgggg caccgccacc tgaccacgca gatcaacttt       720
gctggcgaca gtacctgtg ggacgacttt gcctatgcca cccgcgacgg gctgatcggc       780
gaactgcgtt ttgtcgagga tgcggcgcg gcgcgcgacc gcggtgtgca aggcgagcgc       840
tttgccgagc tgtcattcga cttccgcttg cagggtgcca agtcgcctga cgccgaggcg       900
```
cgaagccatc ggccgcgggc gttgcaggag ggctga 936

<210> SEQ ID NO 7
<211> LENGTH: 174
<212> TYPE: PRT
<213> ORGANISM: Escherichia coli

<400> SEQUENCE: 7

Met Thr Gln Pro Leu Phe Leu Ile Gly Pro Arg Gly Cys Gly Lys Thr
1               5                   10                  15

Thr Val Gly Met Ala Leu Ala Asp Ser Leu Asn Arg Arg Phe Val Asp
            20                  25                  30

Thr Asp Gln Trp Leu Gln Ser Gln Leu Asn Met Thr Val Ala Glu Ile
        35                  40                  45

Val Glu Arg Glu Glu Trp Ala Gly Phe Arg Ala Arg Glu Thr Ala Ala
    50                  55                  60

Leu Glu Ala Val Thr Ala Pro Ser Thr Val Ile Ala Thr Gly Gly Gly
65                  70                  75                  80

Ile Ile Leu Thr Glu Phe Asn Arg His Phe Met Gln Asn Asn Gly Ile
                85                  90                  95

Val Val Tyr Leu Cys Ala Pro Val Ser Val Leu Val Asn Arg Leu Gln
            100                 105                 110

Ala Ala Pro Glu Glu Asp Leu Arg Pro Thr Leu Thr Gly Lys Pro Leu
        115                 120                 125

Ser Glu Glu Val Gln Glu Val Leu Glu Glu Arg Asp Ala Leu Tyr Arg
    130                 135                 140

Glu Val Ala His Ile Ile Asp Ala Thr Asn Glu Pro Ser Gln Val
145                 150                 155                 160

Ile Ser Glu Ile Arg Ser Ala Leu Ala Gln Thr Ile Asn Cys
                165                 170

<210> SEQ ID NO 8
<211> LENGTH: 792
<212> TYPE: PRT
<213> ORGANISM: Escherichia coli

<400> SEQUENCE: 8

Met Ser Asn Asn Gly Ser Ser Pro Leu Val Leu Trp Tyr Asn Gln Leu
1               5                   10                  15

Gly Met Asn Asp Val Asp Arg Val Gly Gly Lys Asn Ala Ser Leu Gly
            20                  25                  30

Glu Met Ile Thr Asn Leu Ser Gly Met Gly Val Ser Val Pro Asn Gly
        35                  40                  45

Phe Ala Thr Thr Ala Asp Ala Phe Asn Gln Phe Leu Asp Gln Ser Gly
    50                  55                  60

Val Asn Gln Arg Ile Tyr Glu Leu Leu Asp Lys Thr Asp Ile Asp Asp
65                  70                  75                  80

Val Thr Gln Leu Ala Lys Ala Gly Ala Gln Ile Arg Gln Trp Ile Ile
                85                  90                  95

Asp Thr Pro Phe Gln Pro Glu Leu Glu Asn Ala Ile Arg Glu Ala Tyr
            100                 105                 110

Ala Gln Leu Ser Ala Asp Asp Glu Asn Ala Ser Phe Ala Val Arg Ser
        115                 120                 125

Ser Ala Thr Ala Glu Asp Met Pro Asp Ala Ser Phe Ala Gly Gln Gln
    130                 135                 140

Glu Thr Phe Leu Asn Val Gln Gly Phe Asp Ala Val Leu Val Ala Val

```
              145                 150                 155                 160
Lys His Val Phe Ala Ser Leu Phe Asn Asp Arg Ala Ile Ser Tyr Arg
                  165                 170                 175

Val His Gln Gly Tyr Asp His Arg Gly Val Ala Leu Ser Ala Gly Val
                  180                 185                 190

Gln Arg Met Val Arg Ser Asp Leu Ala Ser Ser Gly Val Met Phe Ser
                  195                 200                 205

Ile Asp Thr Glu Ser Gly Phe Asp Gln Val Val Phe Ile Thr Ser Ala
              210                 215                 220

Trp Gly Leu Gly Glu Met Val Gln Gly Ala Val Asn Pro Asp Glu
225                 230                 235                 240

Phe Tyr Val His Lys Pro Thr Leu Ala Ala Asn Arg Pro Ala Ile Val
                  245                 250                 255

Arg Arg Thr Met Gly Ser Lys Lys Ile Arg Met Val Tyr Ala Pro Thr
                  260                 265                 270

Gln Glu His Gly Lys Gln Val Lys Ile Glu Asp Val Pro Gln Glu Gln
                  275                 280                 285

Arg Asp Ile Phe Ser Leu Thr Asn Glu Glu Val Gln Glu Leu Ala Lys
              290                 295                 300

Gln Ala Val Gln Ile Glu Lys His Tyr Gly Arg Pro Met Asp Ile Glu
305                 310                 315                 320

Trp Ala Lys Asp Gly His Thr Gly Lys Leu Phe Ile Val Gln Ala Arg
                  325                 330                 335

Pro Glu Thr Val Arg Ser Arg Gly Gln Val Met Glu Arg Tyr Thr Leu
                  340                 345                 350

His Ser Gln Gly Lys Ile Ile Ala Glu Gly Arg Ala Ile Gly His Arg
                  355                 360                 365

Ile Gly Ala Gly Pro Val Lys Val Ile His Asp Ile Ser Glu Met Asn
              370                 375                 380

Arg Ile Glu Pro Gly Asp Val Leu Val Thr Asp Met Thr Asp Pro Asp
385                 390                 395                 400

Trp Glu Pro Ile Met Lys Lys Ala Ser Ala Ile Val Thr Asn Arg Gly
                  405                 410                 415

Gly Arg Thr Cys His Ala Ala Ile Ile Ala Arg Glu Leu Gly Ile Pro
                  420                 425                 430

Ala Val Val Gly Cys Gly Asp Ala Thr Glu Arg Met Lys Asp Gly Glu
                  435                 440                 445

Asn Val Thr Val Ser Cys Ala Glu Gly Asp Thr Gly Tyr Val Tyr Ala
              450                 455                 460

Glu Leu Leu Glu Phe Ser Val Lys Ser Ser Val Glu Thr Met Pro
465                 470                 475                 480

Asp Leu Pro Leu Lys Val Met Asn Val Gly Asn Pro Asp Arg Ala
                  485                 490                 495

Phe Asp Phe Ala Cys Leu Pro Asn Glu Gly Val Gly Leu Ala Arg Leu
                  500                 505                 510

Glu Phe Ile Ile Asn Arg Met Ile Gly Val His Pro Arg Ala Leu Leu
                  515                 520                 525

Glu Phe Asp Asp Gln Glu Pro Gln Leu Gln Asn Glu Ile Arg Glu Met
                  530                 535                 540

Met Lys Gly Phe Asp Ser Pro Arg Glu Phe Tyr Val Gly Arg Leu Thr
545                 550                 555                 560

Glu Gly Ile Ala Thr Leu Gly Ala Ala Phe Tyr Pro Lys Arg Val Ile
                  565                 570                 575
```

```
Val Arg Leu Ser Asp Phe Lys Ser Asn Glu Tyr Ala Asn Leu Val Gly
            580                 585                 590

Gly Glu Arg Tyr Glu Pro Asp Glu Asn Pro Met Leu Gly Phe Arg
            595                 600                 605

Gly Ala Gly Arg Tyr Val Ser Asp Ser Phe Arg Asp Cys Phe Ala Leu
            610                 615                 620

Glu Cys Glu Ala Val Lys Arg Val Arg Asn Asp Met Gly Leu Thr Asn
625                 630                 635                 640

Val Glu Ile Met Ile Pro Phe Val Arg Thr Val Asp Gln Ala Lys Ala
                645                 650                 655

Val Val Glu Glu Leu Ala Arg Gln Gly Leu Lys Arg Gly Glu Asn Gly
            660                 665                 670

Leu Lys Ile Ile Met Met Cys Glu Ile Pro Ser Asn Ala Leu Leu Ala
675                 680                 685

Glu Gln Phe Leu Glu Tyr Phe Asp Gly Phe Ser Ile Gly Ser Asn Asp
            690                 695                 700

Met Thr Gln Leu Ala Leu Gly Leu Asp Arg Asp Ser Gly Val Val Ser
705                 710                 715                 720

Glu Leu Phe Asp Glu Arg Asn Asp Ala Val Lys Ala Leu Leu Ser Met
                725                 730                 735

Ala Ile Arg Ala Ala Lys Lys Gln Gly Lys Tyr Val Gly Ile Cys Gly
            740                 745                 750

Gln Gly Pro Ser Asp His Glu Asp Phe Ala Ala Trp Leu Met Glu Glu
            755                 760                 765

Gly Ile Asp Ser Leu Ser Leu Asn Pro Asp Thr Val Val Gln Thr Trp
            770                 775                 780

Leu Ser Leu Ala Glu Leu Lys Lys
785                 790

<210> SEQ ID NO 9
<211> LENGTH: 663
<212> TYPE: PRT
<213> ORGANISM: Escherichia coli

<400> SEQUENCE: 9

Met Ser Ser Arg Lys Glu Leu Ala Asn Ala Ile Arg Ala Leu Ser Met
1               5                   10                  15

Asp Ala Val Gln Lys Ala Lys Ser Gly His Pro Gly Ala Pro Met Gly
                20                  25                  30

Met Ala Asp Ile Ala Glu Val Leu Trp Arg Asp Phe Leu Lys His Asn
            35                  40                  45

Pro Gln Asn Pro Ser Trp Ala Asp Arg Asp Arg Phe Val Leu Ser Asn
        50                  55                  60

Gly His Gly Ser Met Leu Ile Tyr Ser Leu Leu His Leu Thr Gly Tyr
65                  70                  75                  80

Asp Leu Pro Met Glu Glu Leu Lys Asn Phe Arg Gln Leu His Ser Lys
                85                  90                  95

Thr Pro Gly His Pro Glu Val Gly Tyr Thr Ala Gly Val Glu Thr Thr
            100                 105                 110

Thr Gly Pro Leu Gly Gln Gly Ile Ala Asn Ala Val Gly Met Ala Ile
        115                 120                 125

Ala Glu Lys Thr Leu Ala Ala Gln Phe Asn Arg Pro Gly His Asp Ile
    130                 135                 140

Val Asp His Tyr Thr Tyr Ala Phe Met Gly Asp Gly Cys Met Met Glu
```

-continued

```
            145                 150                 155                 160
Gly Ile Ser His Glu Val Cys Ser Leu Ala Gly Thr Leu Lys Leu Gly
                165                 170                 175
Lys Leu Ile Ala Phe Tyr Asp Asp Asn Gly Ile Ser Ile Asp Gly His
                180                 185                 190
Val Glu Gly Trp Phe Thr Asp Thr Ala Met Arg Phe Glu Ala Tyr
                195                 200                 205
Gly Trp His Val Ile Arg Asp Ile Asp Gly His Asp Ala Ala Ser Ile
                210                 215                 220
Lys Arg Ala Val Glu Glu Ala Arg Ala Val Thr Asp Lys Pro Ser Leu
225                 230                 235                 240
Leu Met Cys Lys Thr Ile Ile Gly Phe Gly Ser Pro Asn Lys Ala Gly
                245                 250                 255
Thr His Asp Ser His Gly Ala Pro Leu Gly Asp Ala Glu Ile Ala Leu
                260                 265                 270
Thr Arg Glu Gln Leu Gly Trp Lys Tyr Ala Pro Phe Glu Ile Pro Ser
                275                 280                 285
Glu Ile Tyr Ala Gln Trp Asp Ala Lys Glu Ala Gly Gln Ala Lys Glu
                290                 295                 300
Ser Ala Trp Asn Glu Lys Phe Ala Ala Tyr Ala Lys Ala Tyr Pro Gln
305                 310                 315                 320
Glu Ala Ala Glu Phe Thr Arg Arg Met Lys Gly Glu Met Pro Ser Asp
                325                 330                 335
Phe Asp Ala Lys Ala Lys Glu Phe Ile Ala Lys Leu Gln Ala Asn Pro
                340                 345                 350
Ala Lys Ile Ala Ser Arg Lys Ala Ser Gln Asn Ala Ile Glu Ala Phe
                355                 360                 365
Gly Pro Leu Leu Pro Glu Phe Leu Gly Gly Ser Ala Asp Leu Ala Pro
                370                 375                 380
Ser Asn Leu Thr Leu Trp Ser Gly Ser Lys Ala Ile Asn Glu Asp Ala
385                 390                 395                 400
Ala Gly Asn Tyr Ile His Tyr Gly Val Arg Glu Phe Gly Met Thr Ala
                405                 410                 415
Ile Ala Asn Gly Ile Ser Leu His Gly Gly Phe Leu Pro Tyr Thr Ser
                420                 425                 430
Thr Phe Leu Met Phe Val Glu Tyr Ala Arg Asn Ala Val Arg Met Ala
                435                 440                 445
Ala Leu Met Lys Gln Arg Gln Val Met Val Tyr Thr His Asp Ser Ile
    450                 455                 460
Gly Leu Gly Glu Asp Gly Pro Thr His Gln Pro Val Glu Gln Val Ala
465                 470                 475                 480
Ser Leu Arg Val Thr Pro Asn Met Ser Thr Trp Arg Pro Cys Asp Gln
                485                 490                 495
Val Glu Ser Ala Val Ala Trp Lys Tyr Gly Val Glu Arg Gln Asp Gly
                500                 505                 510
Pro Thr Ala Leu Ile Leu Ser Arg Gln Asn Leu Ala Gln Gln Glu Arg
                515                 520                 525
Thr Glu Glu Gln Leu Ala Asn Ile Ala Arg Gly Gly Tyr Val Leu Lys
                530                 535                 540
Asp Cys Ala Gly Gln Pro Glu Leu Ile Phe Ile Ala Thr Gly Ser Glu
545                 550                 555                 560
Val Glu Leu Ala Val Ala Ala Tyr Glu Lys Leu Thr Ala Glu Gly Val
                565                 570                 575
```

```
Lys Ala Arg Val Val Ser Met Pro Ser Thr Asp Ala Phe Asp Lys Gln
            580                 585                 590

Asp Ala Ala Tyr Arg Glu Ser Val Leu Pro Lys Ala Val Thr Ala Arg
            595                 600                 605

Val Ala Val Glu Ala Gly Ile Ala Asp Tyr Trp Tyr Lys Tyr Val Gly
610                 615                 620

Leu Asn Gly Ala Ile Val Gly Met Thr Thr Phe Gly Glu Ser Ala Pro
625                 630                 635                 640

Ala Glu Leu Leu Phe Glu Glu Phe Gly Phe Thr Val Asp Asn Val Val
            645                 650                 655

Ala Lys Ala Lys Glu Leu Leu
            660

<210> SEQ ID NO 10
<211> LENGTH: 350
<212> TYPE: PRT
<213> ORGANISM: Escherichia coli

<400> SEQUENCE: 10

Met Asn Tyr Gln Asn Asp Asp Leu Arg Ile Lys Glu Ile Lys Glu Leu
1               5                   10                  15

Leu Pro Pro Val Ala Leu Leu Glu Lys Phe Pro Ala Thr Glu Asn Ala
            20                  25                  30

Ala Asn Thr Val Ala His Ala Arg Lys Ala Ile His Lys Ile Leu Lys
        35                  40                  45

Gly Asn Asp Asp Arg Leu Leu Val Val Ile Gly Pro Cys Ser Ile His
50                  55                  60

Asp Pro Val Ala Ala Lys Glu Tyr Ala Thr Arg Leu Leu Ala Leu Arg
65                  70                  75                  80

Glu Glu Leu Lys Asp Glu Leu Glu Ile Val Met Arg Val Tyr Phe Glu
                85                  90                  95

Lys Pro Arg Thr Thr Val Gly Trp Lys Gly Leu Ile Asn Asp Pro His
            100                 105                 110

Met Asp Asn Ser Phe Gln Ile Asn Asp Gly Leu Arg Ile Ala Arg Lys
        115                 120                 125

Leu Leu Leu Asp Ile Asn Asp Ser Gly Leu Pro Ala Ala Gly Glu Phe
130                 135                 140

Leu Asp Met Ile Thr Pro Gln Tyr Leu Ala Asp Leu Met Ser Trp Gly
145                 150                 155                 160

Ala Ile Gly Ala Arg Thr Thr Glu Ser Gln Val His Arg Glu Leu Ala
                165                 170                 175

Ser Gly Leu Ser Cys Pro Val Gly Phe Lys Asn Gly Thr Asp Gly Thr
            180                 185                 190

Ile Lys Val Ala Ile Asp Ala Ile Asn Ala Ala Gly Ala Pro His Cys
        195                 200                 205

Phe Leu Ser Val Thr Lys Trp Gly His Ser Ala Ile Val Asn Thr Ser
210                 215                 220

Gly Asn Gly Asp Cys His Ile Ile Leu Arg Gly Gly Lys Glu Pro Asn
225                 230                 235                 240

Tyr Ser Ala Lys His Val Ala Glu Val Lys Glu Gly Leu Asn Lys Ala
                245                 250                 255

Gly Leu Pro Ala Gln Val Met Ile Asp Phe Ser His Ala Asn Ser Ser
            260                 265                 270

Lys Gln Phe Lys Lys Gln Met Asp Val Cys Ala Asp Val Cys Gln Gln
```

-continued

```
            275                 280                 285
Ile Ala Gly Gly Glu Lys Ala Ile Ile Gly Val Met Val Glu Ser His
            290                 295                 300
Leu Val Glu Gly Asn Gln Ser Leu Glu Ser Gly Glu Pro Leu Ala Tyr
305                 310                 315                 320
Gly Lys Ser Ile Thr Asp Ala Cys Ile Gly Trp Glu Asp Thr Asp Ala
                325                 330                 335
Leu Leu Arg Gln Leu Ala Asn Ala Val Lys Ala Arg Arg Gly
                340                 345                 350
```